US011607315B2

(12) United States Patent
White et al.

(10) Patent No.: US 11,607,315 B2
(45) Date of Patent: Mar. 21, 2023

(54) ADJUSTABLE PRE-SUTURED ALLOGRAFT CONSTRUCT

(71) Applicant: ALLOSOURCE, Centennial, CO (US)

(72) Inventors: Brian White, Denver, CO (US); Christopher Irons, Castle Rock, CO (US); Ruth Bledsoe, Parker, CO (US); Marina Bull, Highlands Ranch, CO (US); Kenneth Blood, Littleton, CO (US)

(73) Assignee: Allosource, Centennial, CO (US)

( * ) Notice: Subject to any disclaimer, the term of this patent is extended or adjusted under 35 U.S.C. 154(b) by 0 days.

(21) Appl. No.: 17/712,430

(22) Filed: Apr. 4, 2022

(65) Prior Publication Data

US 2022/0313441 A1    Oct. 6, 2022

Related U.S. Application Data

(60) Provisional application No. 63/169,991, filed on Apr. 2, 2021.

(51) Int. Cl.
*A61F 2/30* (2006.01)
*A61L 27/36* (2006.01)

(52) U.S. Cl.
CPC ...... *A61F 2/30756* (2013.01); *A61L 27/3612* (2013.01); *A61L 27/3654* (2013.01); *A61F 2002/3055* (2013.01); *A61F 2002/30461* (2013.01)

(58) Field of Classification Search
CPC ..... A61F 2/30756; A61F 2/08; A61L 27/3654
See application file for complete search history.

(56) References Cited

U.S. PATENT DOCUMENTS

| 9,504,557 | B1 | 11/2016 | Samaniego et al. |
| 2001/0018619 | A1 | 8/2001 | Enzerink et al. |
| 2008/0281422 | A1 | 11/2008 | Schmieding |
| 2021/0244403 | A1 | 8/2021 | Lombardo |

FOREIGN PATENT DOCUMENTS

WO    2017/160301 A1    9/2017

OTHER PUBLICATIONS

International Search Report and Written Opinion issued for PCT/US2022/023272, dated Jun. 16, 2022, 9 pp.

*Primary Examiner* — Jason-Dennis N Stewart
(74) *Attorney, Agent, or Firm* — James A. Sheridan; Sheridan Law, LLC

(57) ABSTRACT

A pre-sutured allograft construct and method of manufacture for repairing, replacing, reconstructing, or augmenting a hip or shoulder labrum may include a folded tissue portion extending from a first end to a second end and forming top, middle, and bottom folds. A stitched pattern secures the folded tissue portion into a graft roll having an overall length extending from a first adjustable region, through a central region, and through a second adjustable region. A continuous series of whip stitches extends from the first adjustable region, through the central region, and through the second adjustable region. A series of triple circumferential stitches overlays the whip stitches in the first and the second adjustable regions, while a series of circumferential stitches alternates with the whip stitches in the central region. The construct is pre-manufactured as an allograft product, but is adjustable during the surgical procedure within the body. Other embodiments are also disclosed.

22 Claims, 28 Drawing Sheets

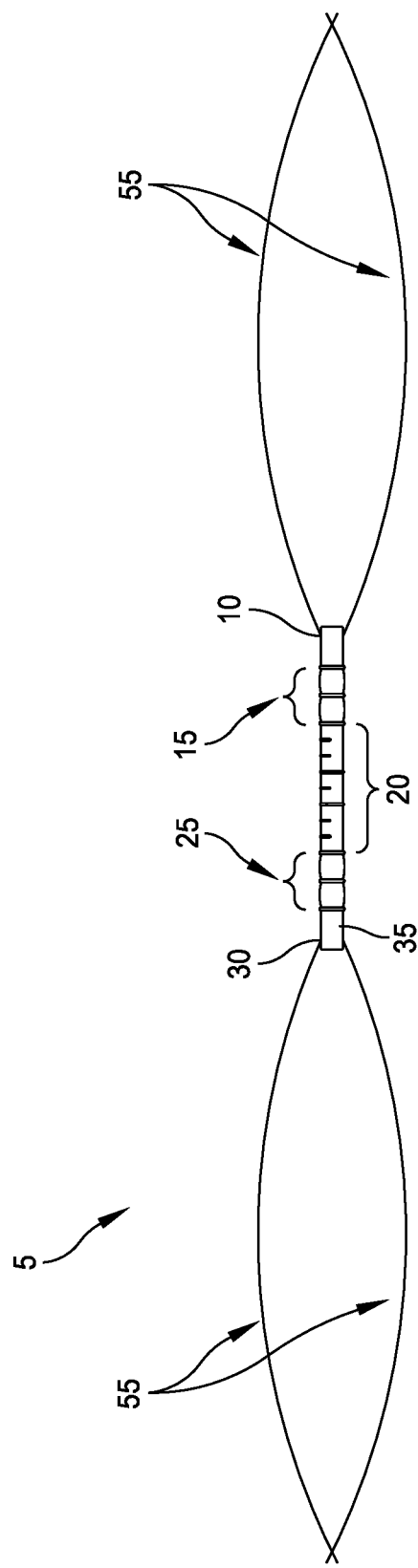

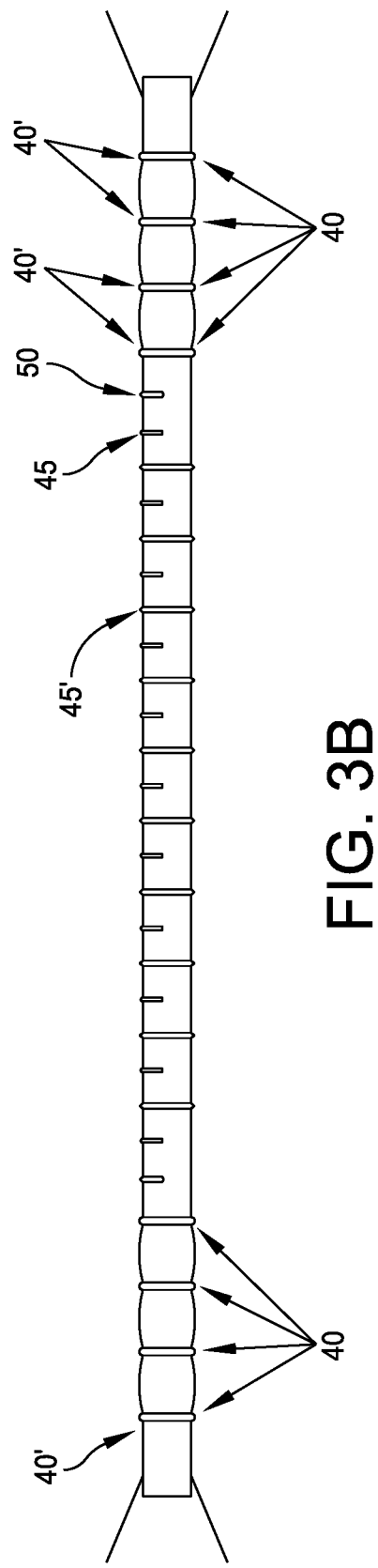

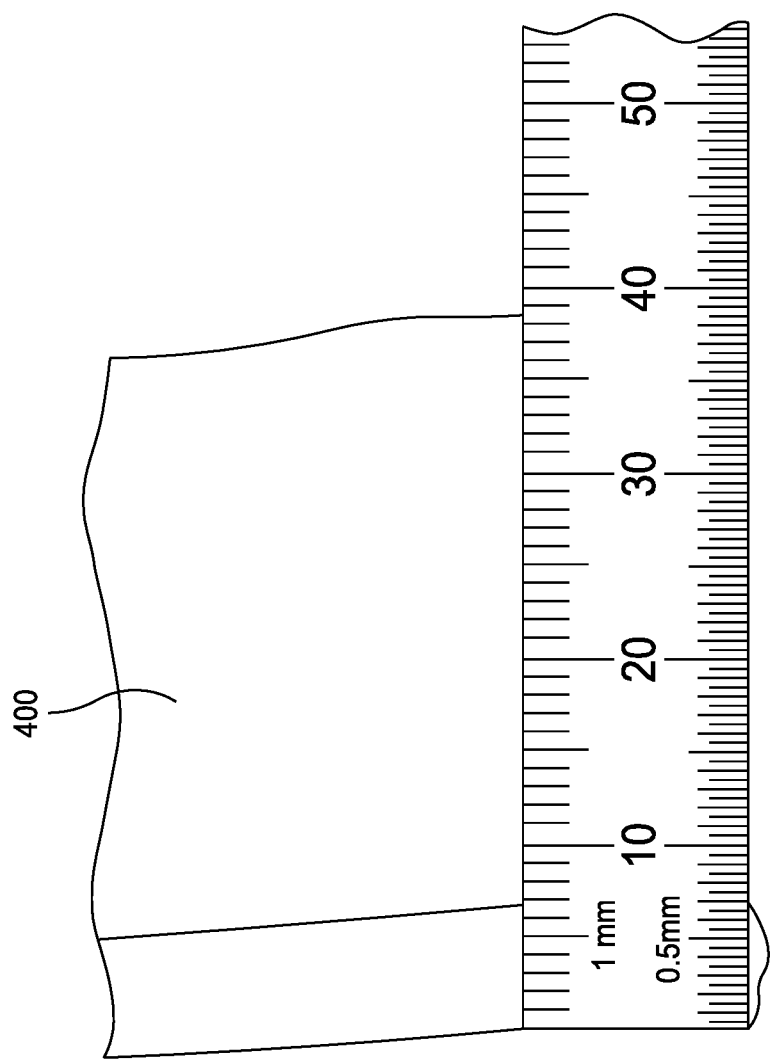

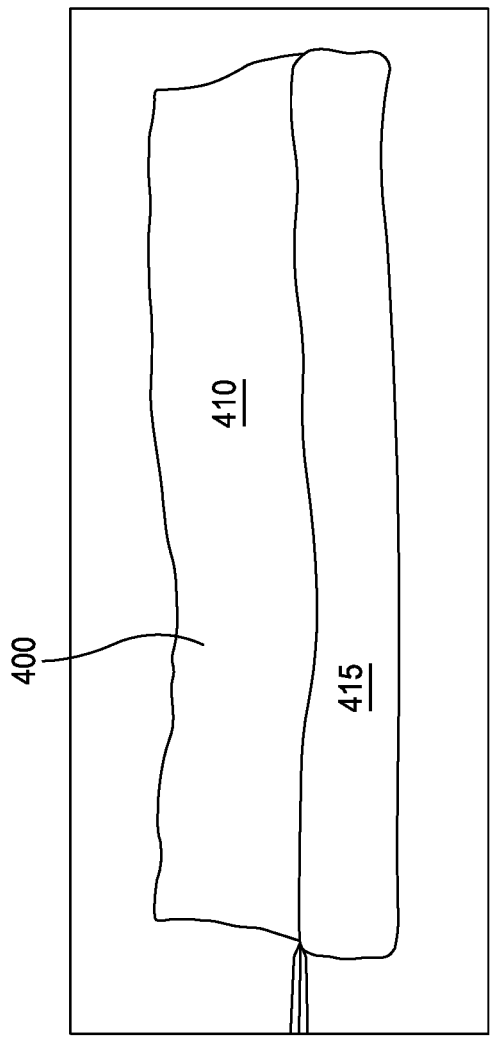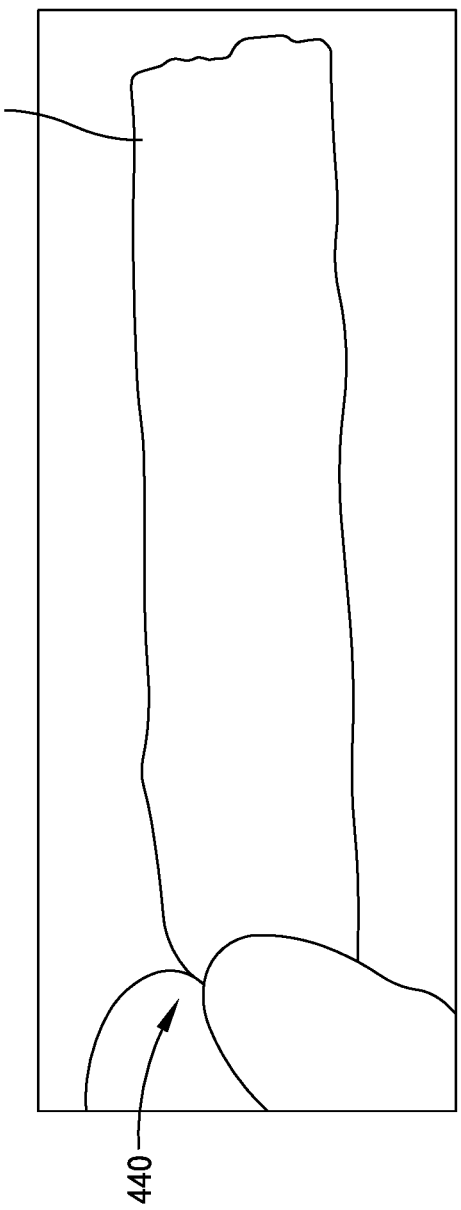

ADJUSTABLE PRE-SUTURED ALLOGRAFT CONSTRUCT

REFERENCE TO PENDING PRIOR PATENT APPLICATION

This application claims the benefit under 35 U.S.C. 119 (e) of U.S. Provisional Patent Application No. 63/169,991, filed Apr. 2, 2021 by Ruth Bledsoe, et al., for "SOFT TISSUE CONSTRUCT FOR SURGICAL USE AND METHOD OF MAKING THEREOF," which patent application is hereby incorporated herein by reference.

BACKGROUND

An allograft includes bone, tendon, ligament, fascia, skin, or other types of tissue transplanted from one person to another. Allografts are used in a variety of medical treatments, such as knee and other joint replacements, repairs, or augmentations, bone grafts, spinal fusions, eye surgery, and skin grafts for the severely burned. Allografts come from voluntarily donated human tissue obtained from deceased donor-derived, living-related, or living-unrelated donors and can help patients regain mobility, restore function, enjoy a better quality of life, and even save lives.

The labrum is a soft-tissue structure that lines and reinforces the ball-and-socket joint of the shoulder and the hip. When the labrum is torn, frayed, or otherwise damaged as a result of injury, femoroacetabular impingement, or oftentimes as part of the aging process, a substitute fascia or soft-tissue graft may be used to surgically repair, replace, or augment the damaged labrum.

Traditionally, a surgeon must accurately determine the required length of allograft fascia needed to replace the damaged portion of the patient's labrum (segmental or circumferential) prior to inserting the prepared graft into the joint space. In addition, the preparation of the fascia graft is a labor-intensive undertaking for surgeons, meticulously suturing the graft to ensure a proper length, cross-sectional diameter, and maintaining the graft's rigidity for each patient and/or circumstance, during the surgical procedure. These techniques are complex and time consuming and difficult to achieve both repeatedly and consistently.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides a pre-sutured allograft construct for repairing, replacing, reconstructing, or augmenting a patient's labrum. The construct may include: (1) a folded tissue portion extending from a first end to a second end, the folded tissue portion forming a top fold, a middle fold, and a bottom fold; and (2) a stitched pattern securing the folded tissue portion into a graft roll having an overall length extending from a first adjustable region, through a central region, and through a second adjustable region, an adjustable length, and a fixed diameter, wherein: (a) a continuous series of whip stitches extends from the first adjustable region, through the central region, and through the second adjustable region; (b) a series of triple circumferential stitches overlays the continuous series of the whip stitches in the first and the second adjustable regions; and (c) a series of circumferential stitches alternates with the continuous series of the whip stitches in the central region. The fixed diameter may be between 5.0 mm and 5.5 mm or 5.5 mm and 6.0 mm. The overall length may be approximately 6 cm, 10 cm, or 14 cm, and the adjustable length may be between 4 cm and 6 cm, 6 cm and 10 cm, or 10 cm and 14 cm.

Another embodiment provides a pre-sutured allograft construct for repairing, replacing, reconstructing, or augmenting a patient's labrum. The construct may include: (1) a tissue roll extending from a first end to a second end, the tissue roll including a top fold, a middle fold, and a bottom fold; and (2) a stitched pattern securing the tissue roll, the stitched pattern extending from a first adjustable region, through a central region, and through a second adjustable region, wherein: (a) each of the first and the second adjustable regions comprises a series of triple circumferential stitches directly overlaying a corresponding series of whip stitches; and (b) the central region comprises a series of circumferential stitches alternating with the series of the whip stitches.

Still another embodiment provides a pre-sutured allograft construct for repairing, replacing, reconstructing, or augmenting a patient's labrum. The construct may include: (1) a tissue roll extending from a first end to a second end; and (2) a stitched pattern securing the tissue roll, the stitched pattern extending through an adjustable region and an adjacent region, wherein: (a) the adjustable region comprises a series of triple circumferential stitches directly overlaying a corresponding series of whip stitches; and (b) the adjacent region comprises a series of circumferential stitches alternating with the series of the whip stitches.

Other embodiments are also disclosed.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which:

FIGS. 1A-1B illustrate respective top and detail views of a small sized embodiment of a pre-sutured allograft construct;

FIGS. 3A-3B illustrate respective top and detail views of a large sized embodiment of a pre-sutured allograft construct;

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

Various embodiments of the systems and methods described herein relate to a pre-sutured, soft-tissue matrix allograft construct, or a pre-sutured construct, for the surgical replacement, reconstruction, repair, and/or augmentation of the labrum due to defects and tears resulting from injury, degeneration, trauma, or disease. The pre-sutured constructed is designed for placement into a labrum area that has been resected, filling the area where tissue has been removed or augmenting/repairing damaged labrum by reinforcement. Embodiments of the pre-sutured construct provide the surgeon practitioner with a mechanism to restore function and support after surgical intervention, improving the life of the patient while reducing operating time and complexity. In addition to reducing operating time with the patient on the operating table, a surgeon may work alone, without a second set of hands, to help with customization of the pre-sutured construct.

Embodiments of the pre-sutured construct may be formed from soft tissues such as, for example, fascia, tendon, or iliotibial band and may be pre-sutured into a cylindrical shape for ease of use. Embodiments of the pre-sutured construct may include three adjustable lengths (e.g., small, medium, large), each provided in two diameters to cover all potential requirements for replacement, repair, reconstruction, or augmentation of the labrum. The standard lengths cover segmental and circumferential procedures.

Embodiments of pre-sutured construct feature a pre-sutured pattern of whip and circumferential stitches that form five regions along a length of the allograft construct: two opposing end regions disposed at the outermost ends of the allograft construct, two opposing adjustable regions disposed adjacent to and inward from the end regions, and one non-adjustable central region disposed between the two adjustable regions. The suture pattern and associated suturing method result in a pre-sutured allograft construct that holds its shape such that it may be pre-sutured and manufactured as a sterile allograft construct product the surgeon orders, rather than sutures or prepares during the surgical procedure, and that features an adjustable length that may be adjusted prior or during the surgical procedure while it is being placed in the surgical site.

Figure 1B:
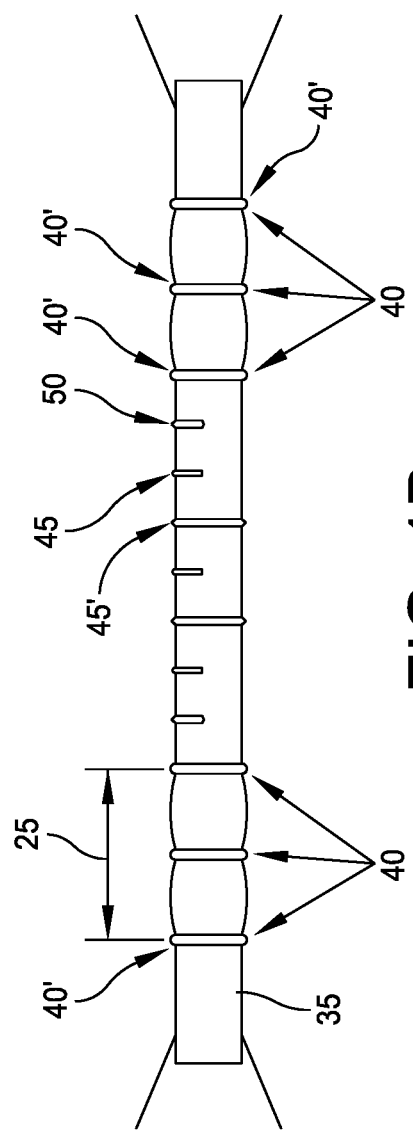

Turning to exemplary embodiments, FIGS. 1A-1B illustrate top and detail views of one embodiment of a pre-sutured construct 5. In this embodiment and as shown in FIG. 1A, the pre-sutured construct 5 has five regions moving from right to left, namely a first end region 10, a first adjustable region 15, a central region 20, a second adjustable region 25, and a second end region 30.

The pre-sutured construct 5 may be formed from an appropriate soft tissue 35 such as, for example, fascia, tendon, or iliotibial band, and may be manufactured in two diameters, a first diameter range of 5.0-5.5 mm and a second diameter range of 5.5-6.0 mm. In this embodiment, the pre-sutured construct 5 is shown having a short length, or a length of approximately 80 mm end-to-end, with an approximate 40 mm central region and 60 mm extending between the start of the first adjustable region 15 and the end of the second adjustable region 25, rendering the short pre-sutured construct 5 adjustable between approximately 40 mm and 60 mm. As shown in FIG. 1B, and as discussed in detail below, the first and the second adjustable regions 15, 25 may each comprise a series of whip and triple circumferential stitches 40, 40', while the central region 20 may comprise an alternating series of whip and central circumferential stitches 45, 45' bounded on each end by a partial circumferential stitch 50.

Figure 2A:
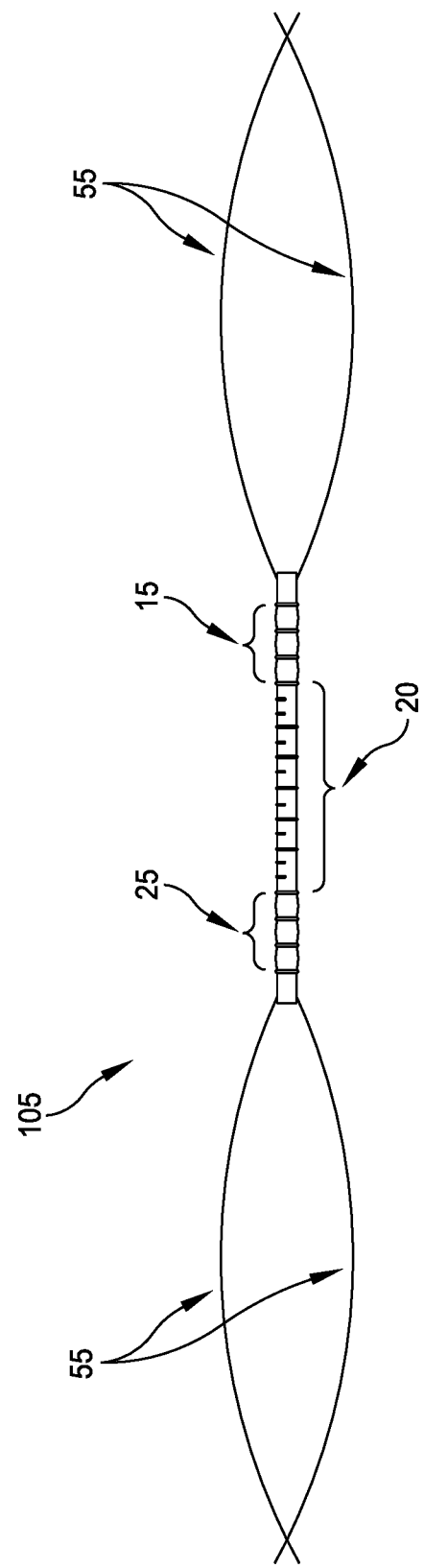
FIGS. 2A-2B illustrate respective top and detail views of a medium sized embodiment of a pre-sutured allograft construct.
Figure 2B:
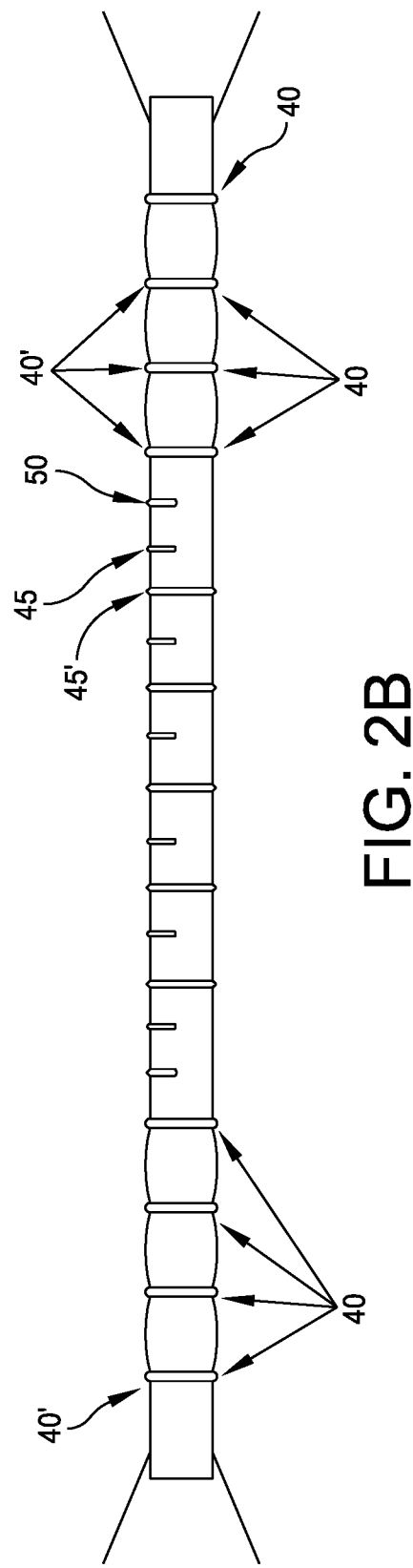
Figure 3A:
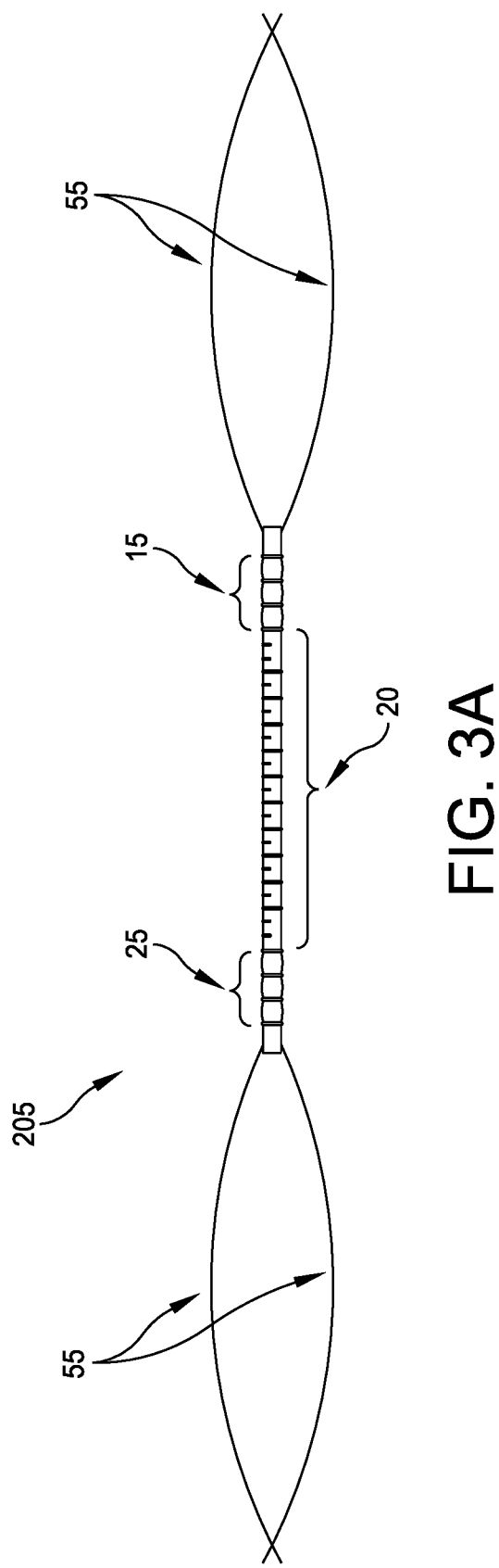

Embodiments of the pre-sutured construct may be manufactured in any reasonable and/or appropriate lengths so as to be applicable to all the potential requirements for replacement, repair, reconstruction, or augmentation of a labrum. For example, FIGS. 2A-2B illustrate a pre-sutured construct 105 in a medium length of approximately 120 mm end-to-end, with an approximate 60 mm length of central region 20 and 100 mm extending between the start of the first adjustable region 15 and the end of the second adjustable region 25, rendering the medium pre-sutured construct 105 adjustable between approximately 60 mm and 100 mm. FIGS. 3A-3B illustrate a pre-sutured construct 205 in a large length of approximately 160 mm from end-to-end, with an approximate 100 mm length of central region 20 and 140 mm extending between the start of the first adjustable region 15 and the end of the second adjustable region 25, rendering the large pre-sutured construct 205 with an adjustable length between approximately 100 mm and 140 mm. In preparing the various lengths of the pre-sutured construct, the triple circumferential stitches 40' of the first and the second adjustable regions 15, 25 and the alternating series of whip and central circumferential stitches 45, 45' of the central region 20 may be repeated in any appropriate numbers, as appropriate and/or necessary, to achieve the desired length of each region. The medium pre-sutured construct 105 and large pre-sutured construct 205 may also be provided in two diameters of 5.0-5.5 mm and 5.5-6.0 mm, respectively.

Figure 4B:
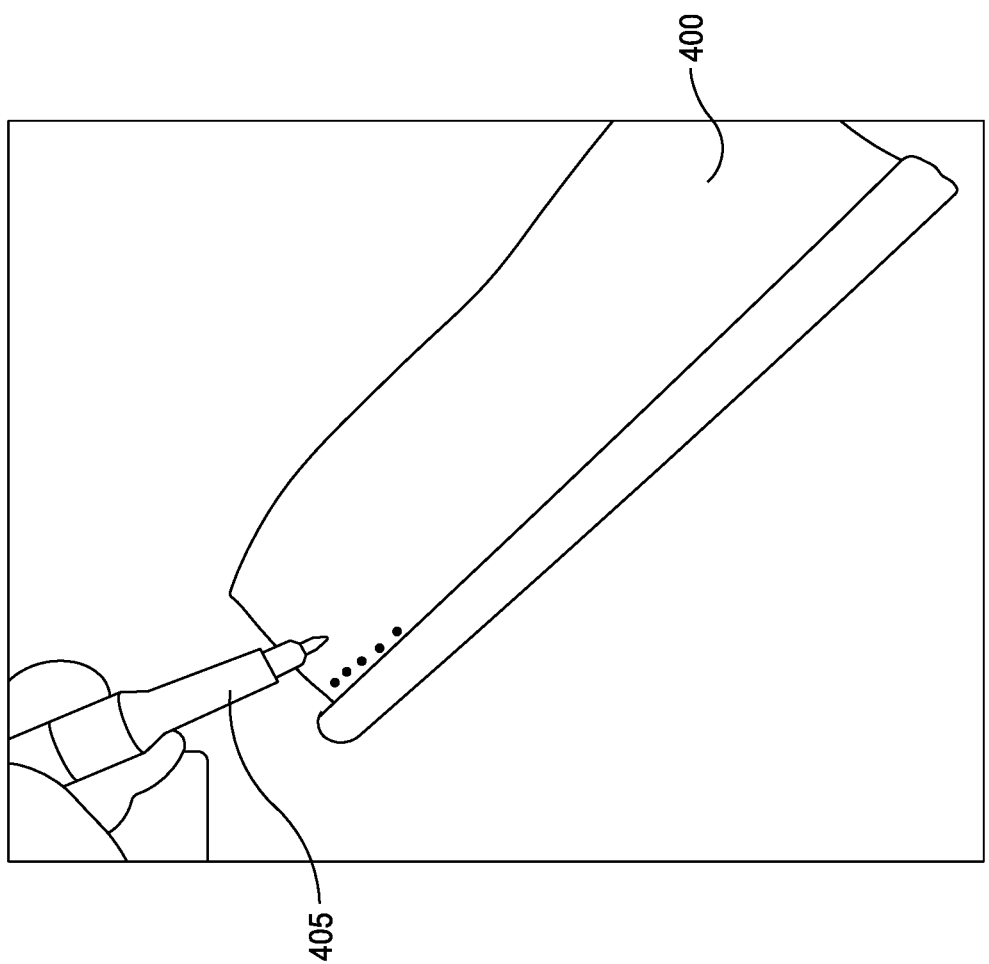
FIGS. 4A-4Z and 4AA illustrate the steps of an exemplary method of manufacturing the embodiments of the pre-sutured allograft construct of FIGS. 1A-1B, 2A-2B, and 3A-3B.
Figure 4C:
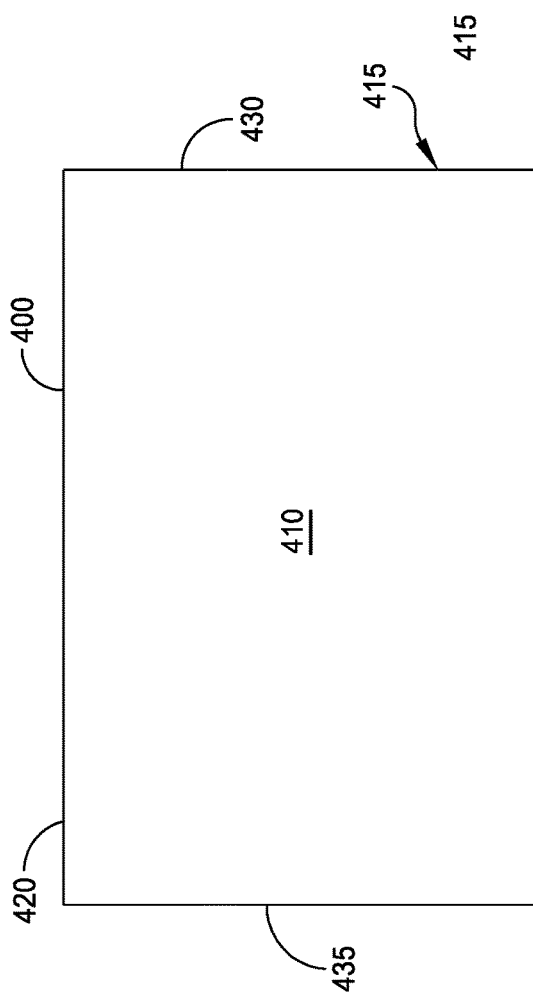
Figure 4E:
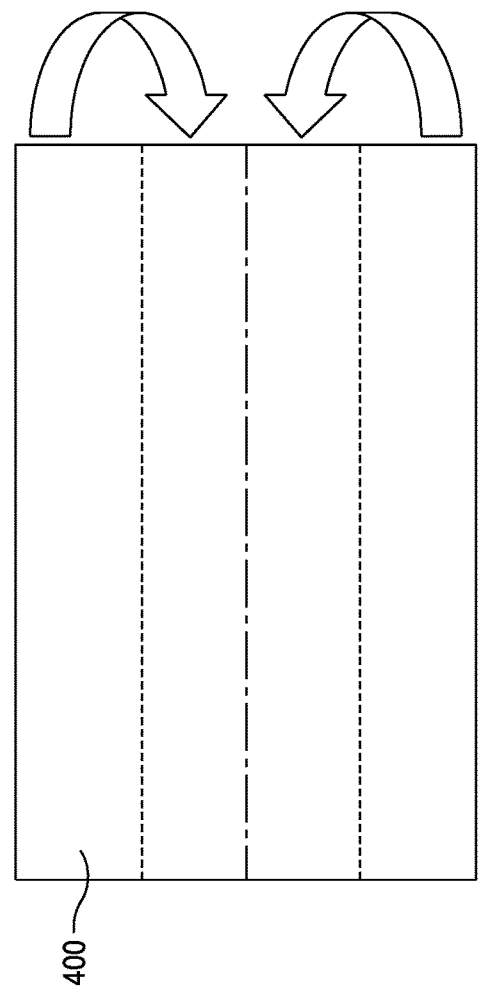
Figure 4H:
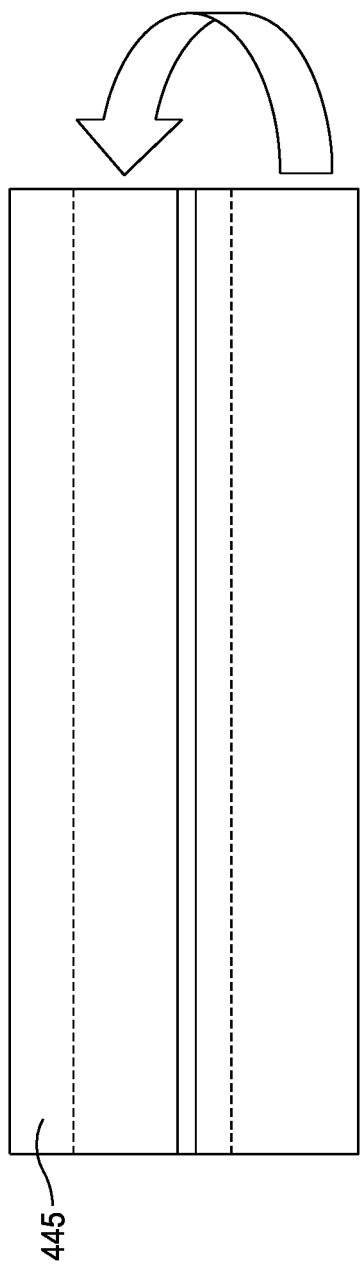
Figure 4I:
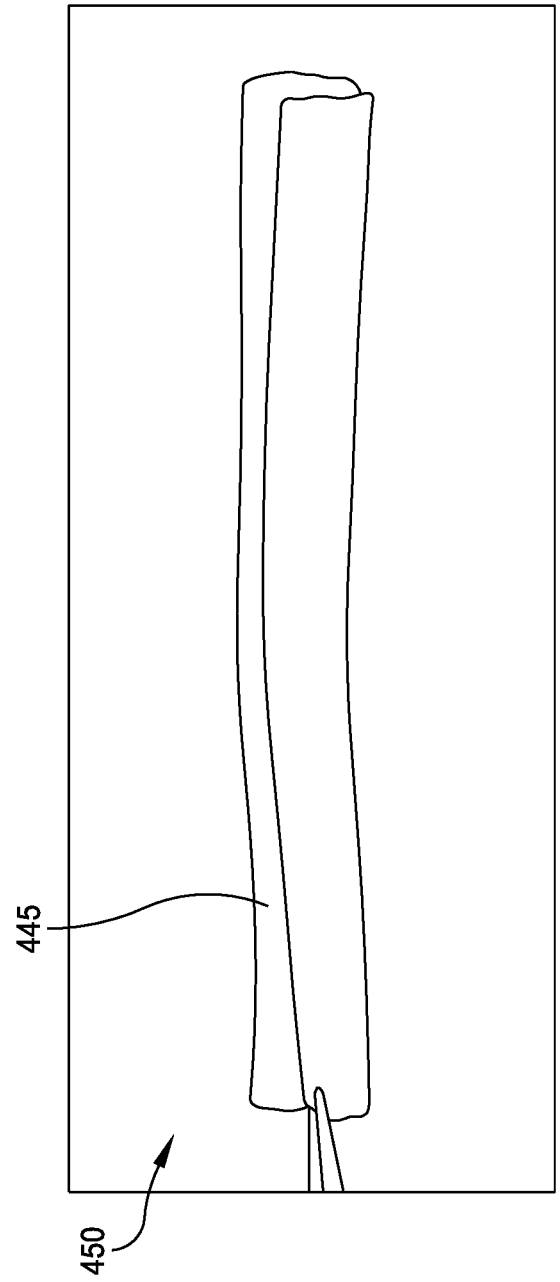
Figure 4J:
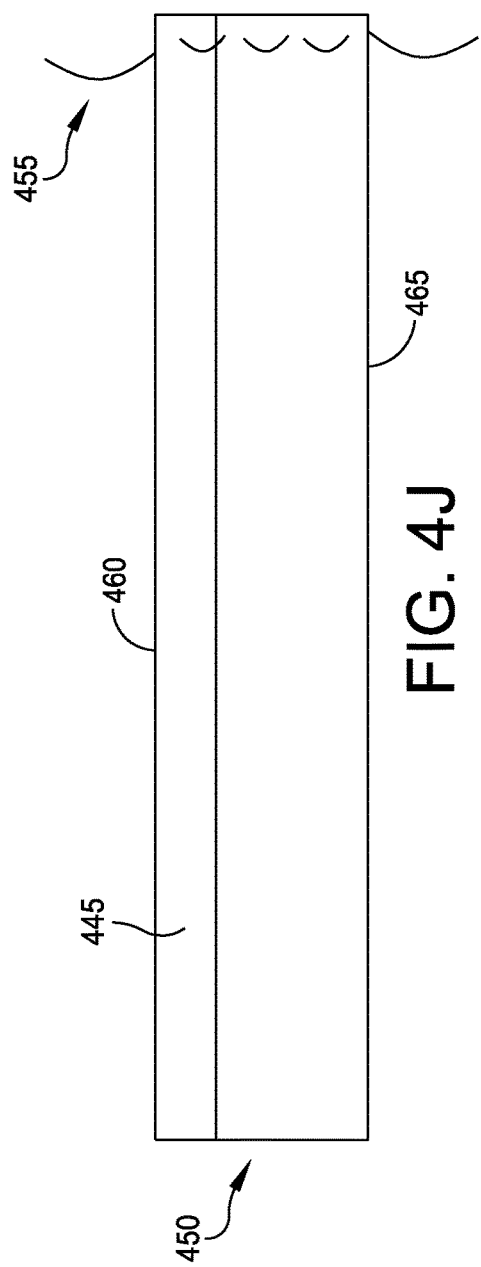
Figure 4K:
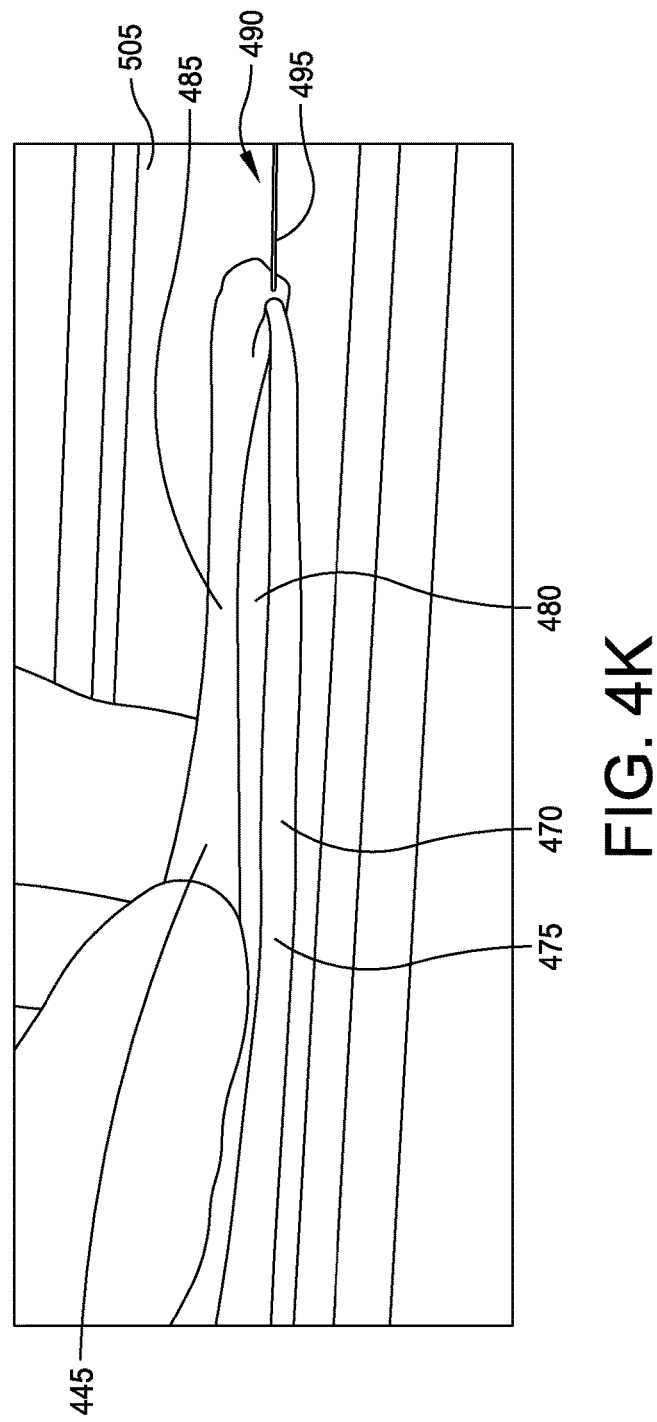
Figure 4L:
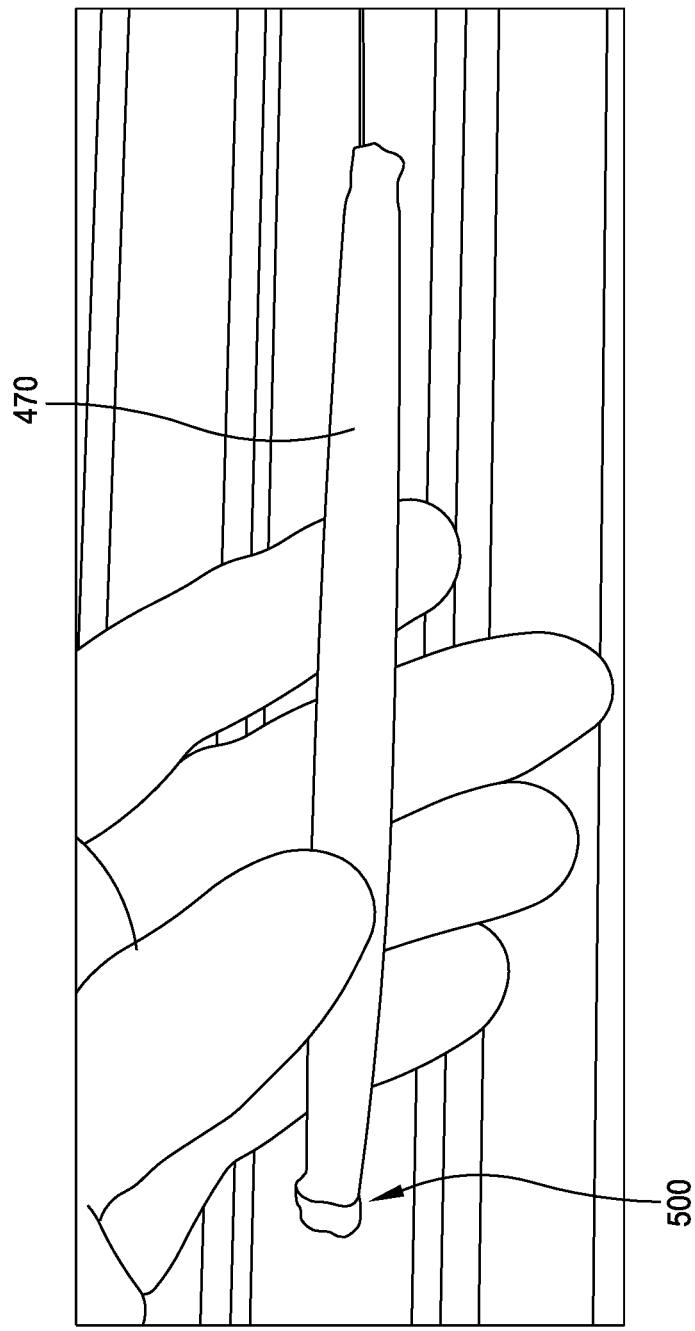
Figure 4M:
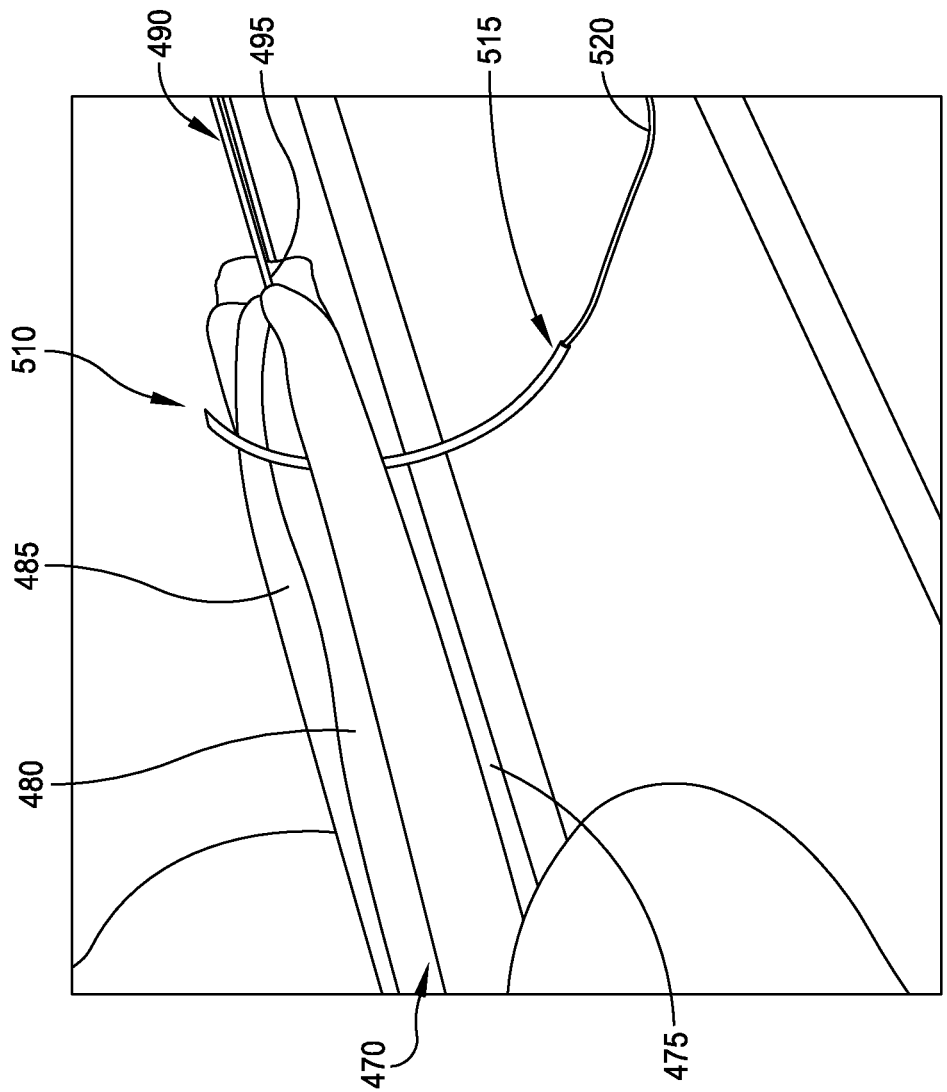
Figure 4N:
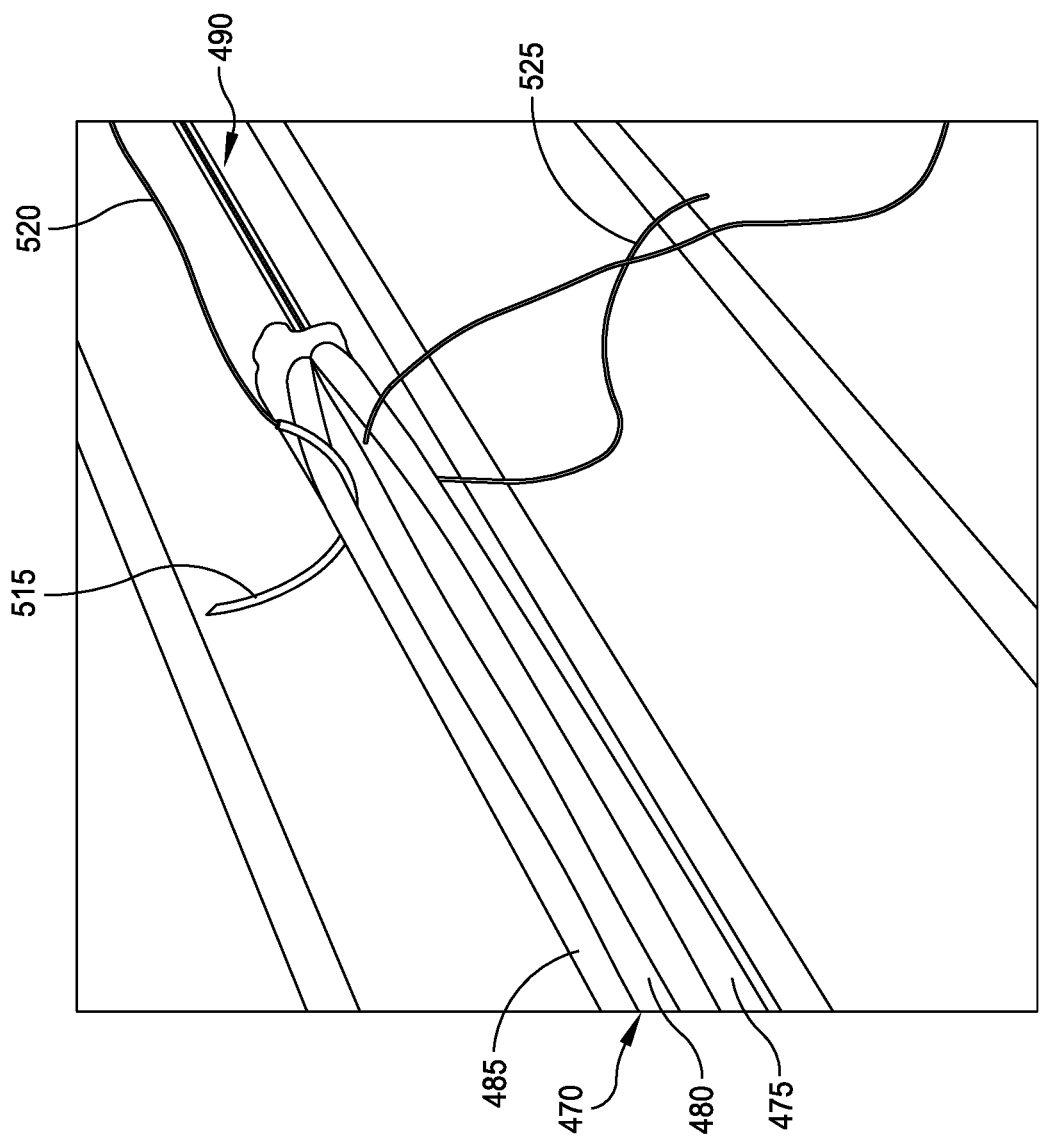
Figure 40:
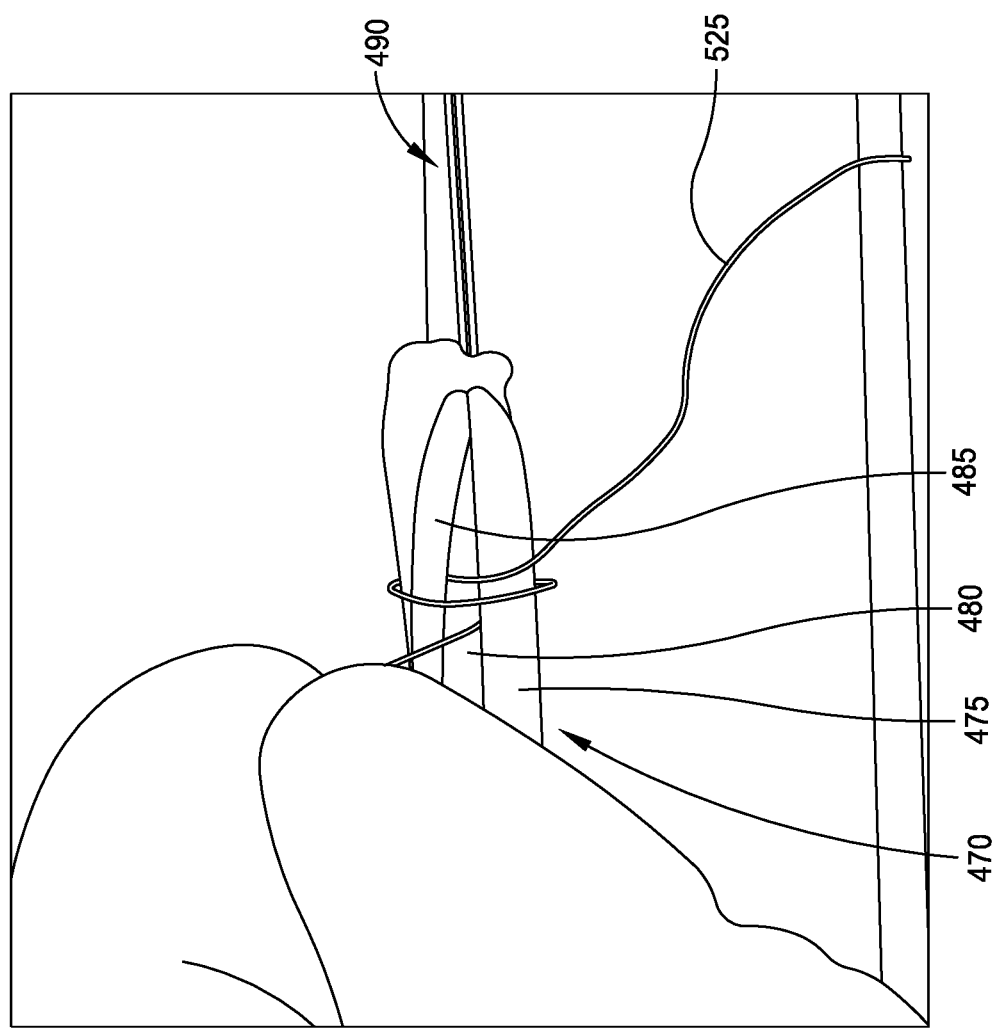
Figure 4P:
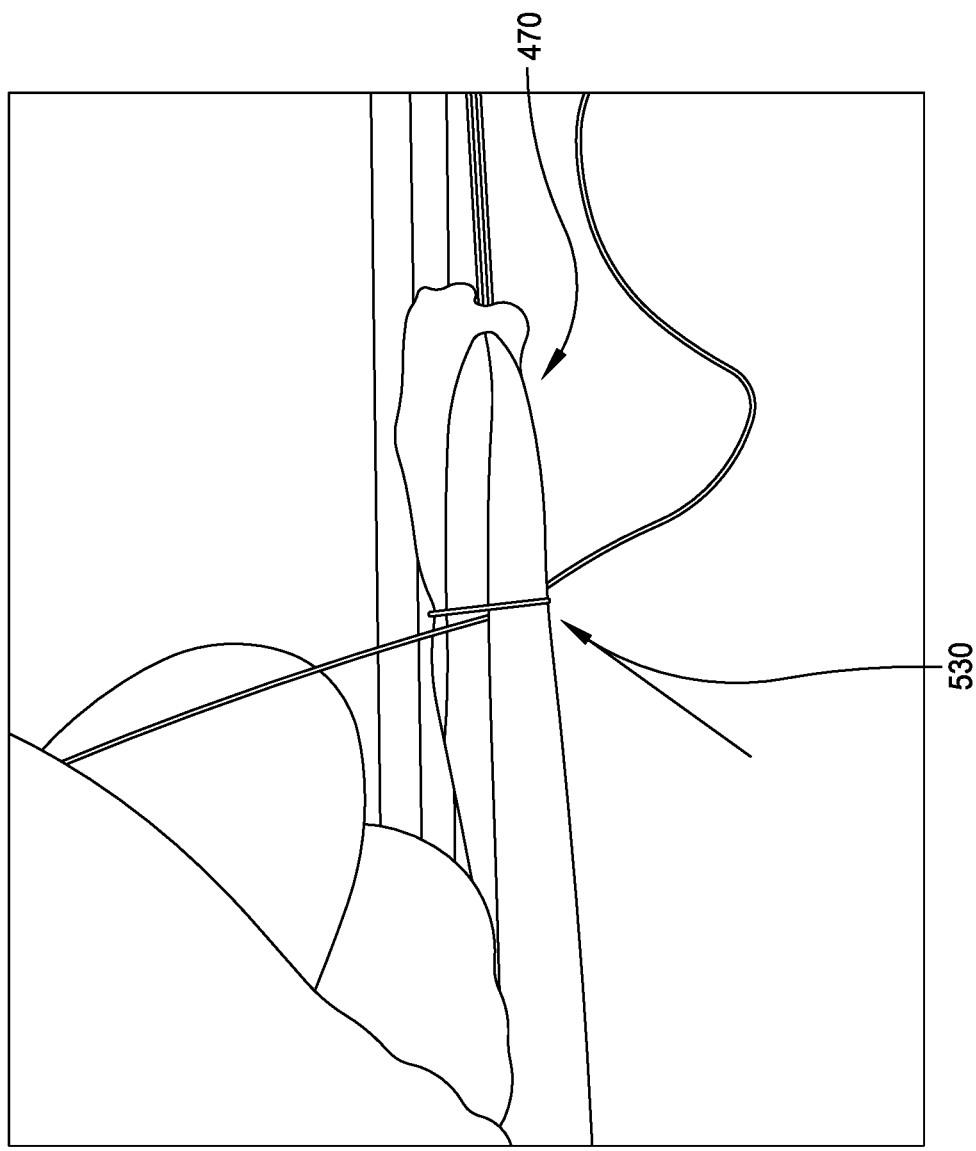
Figure 4Q:
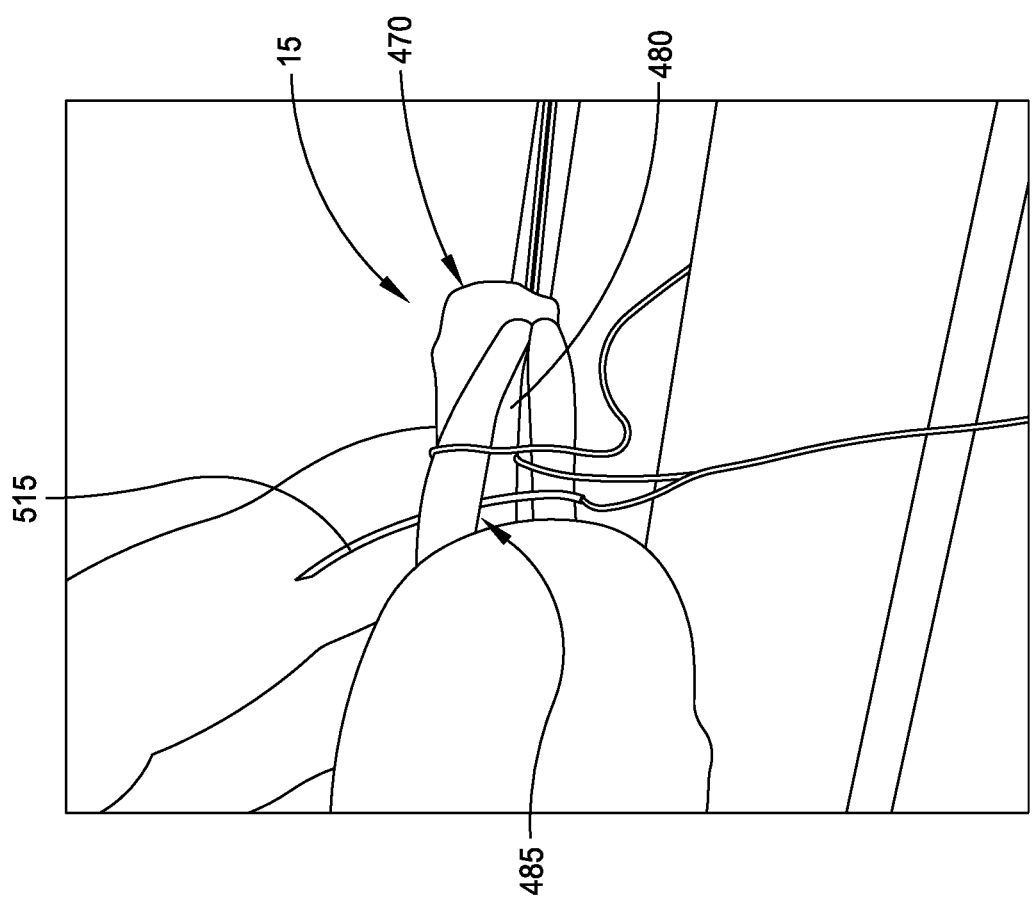
Figure 4R:
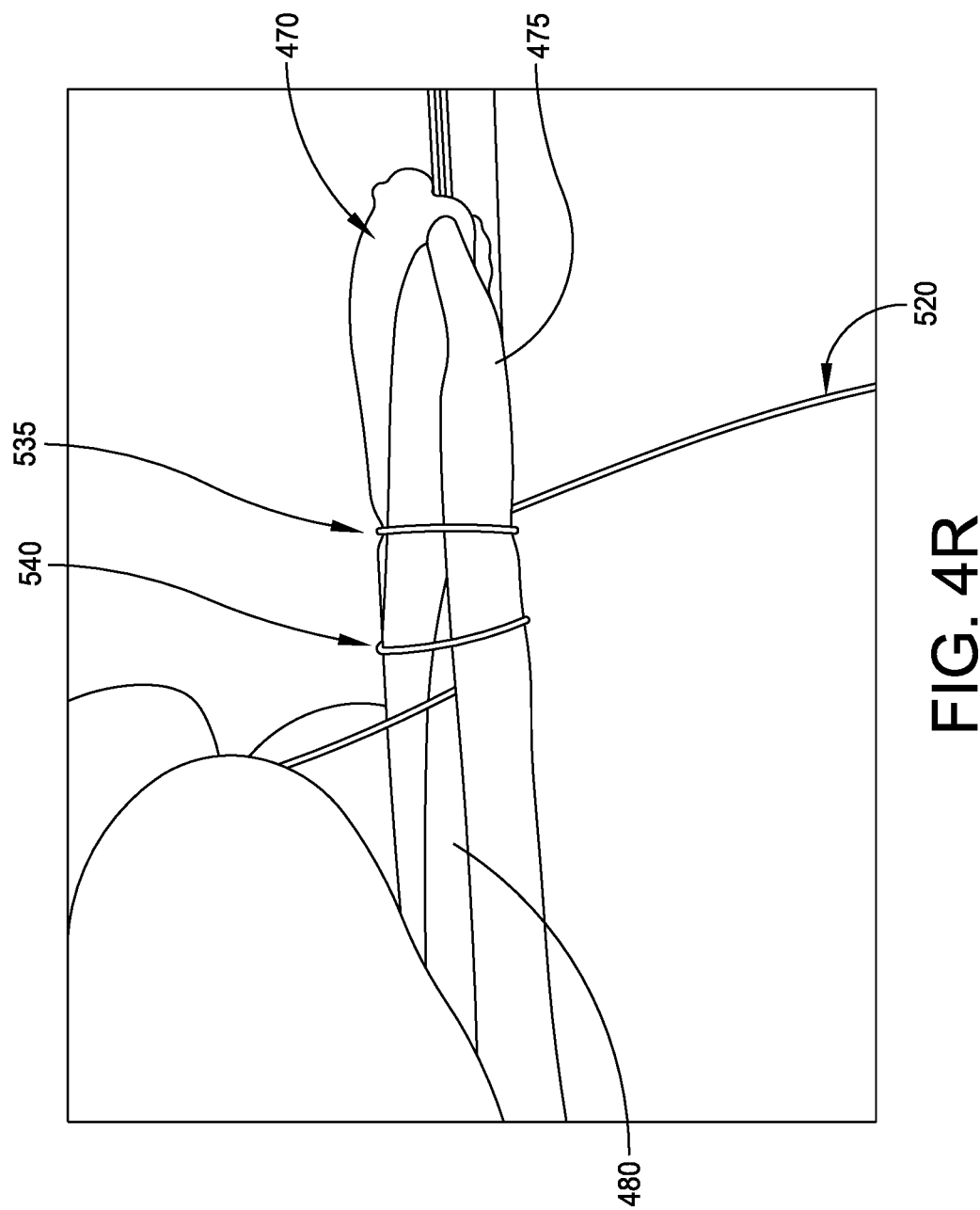
Figure 4S:
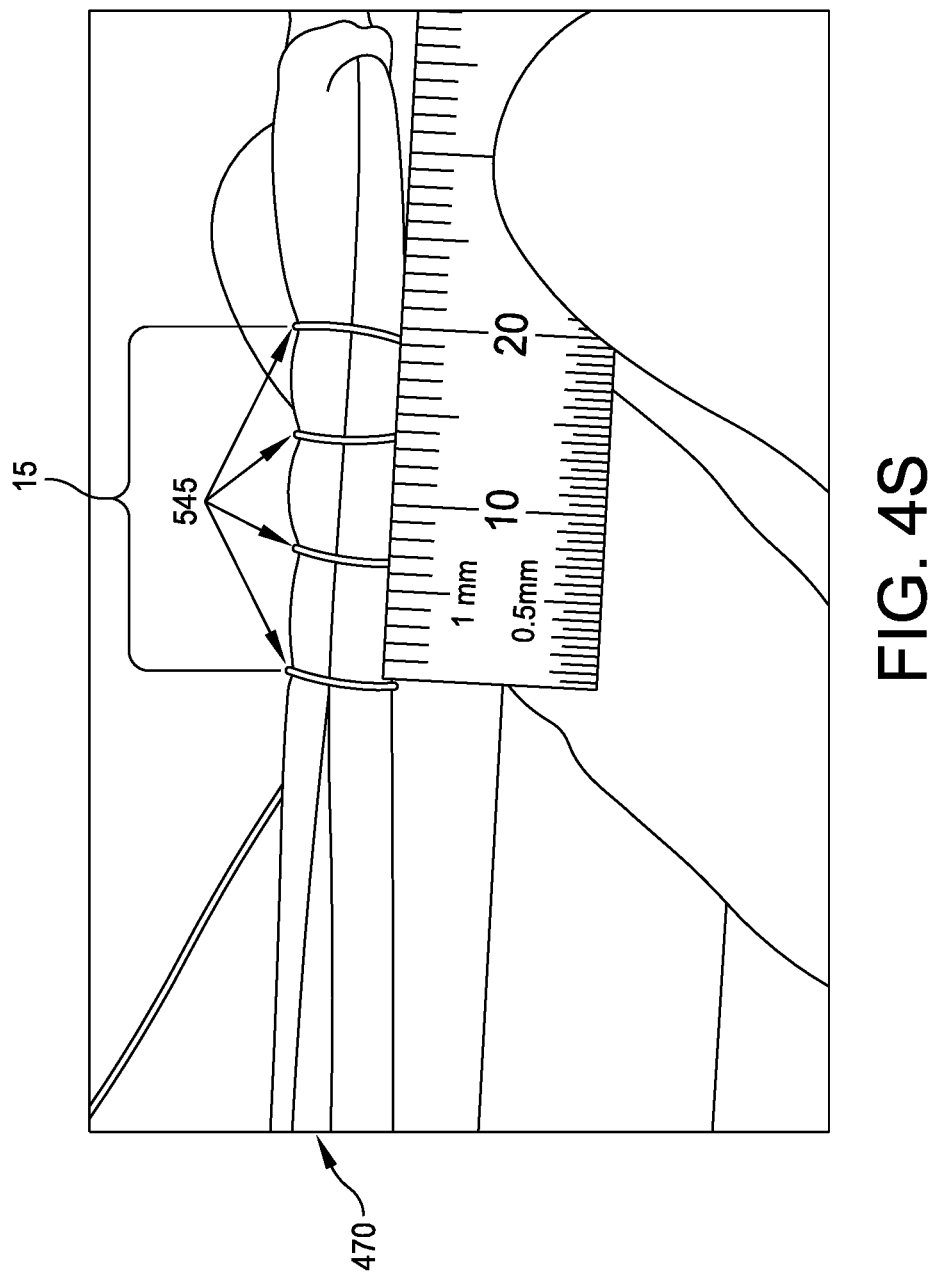
Figure 4T:
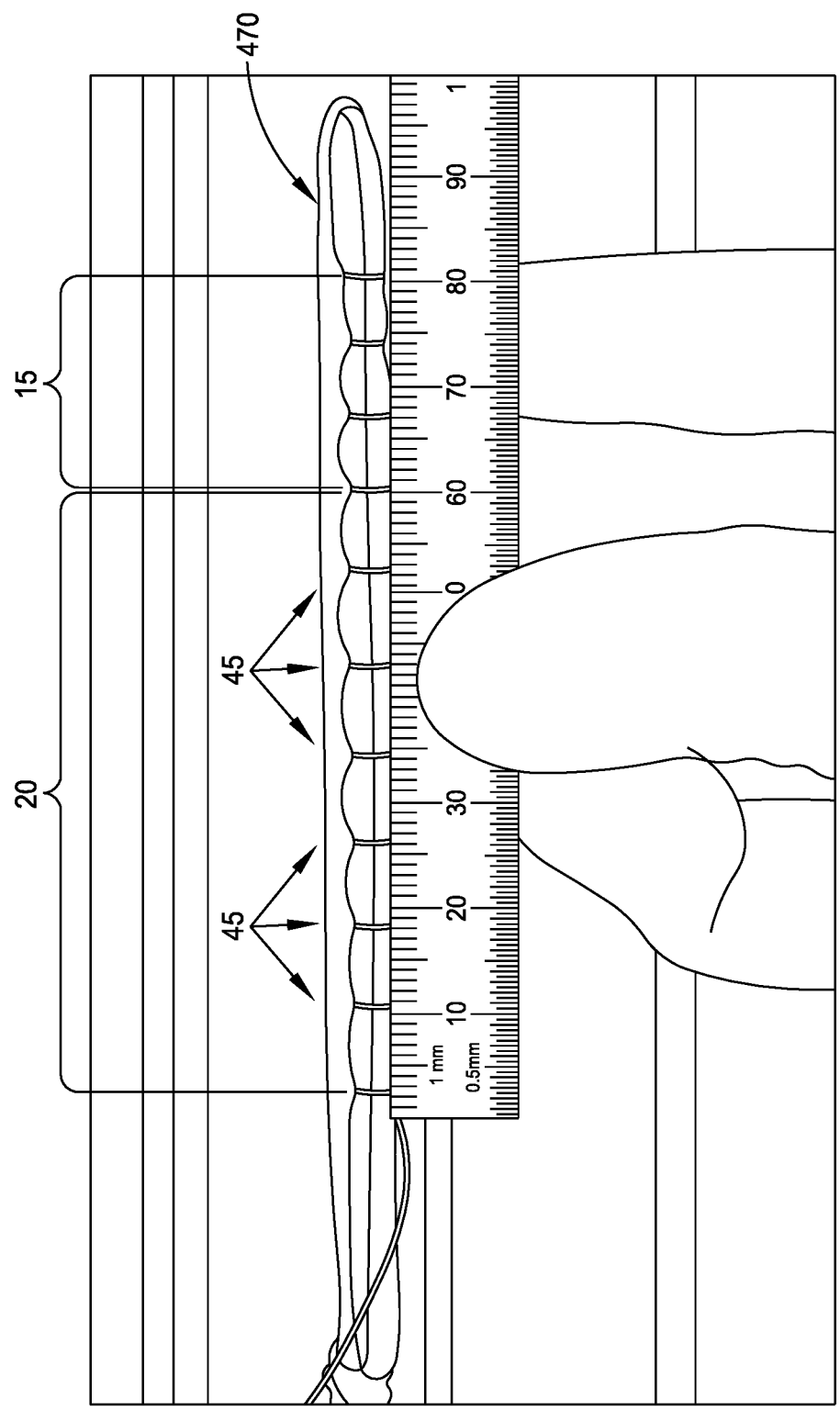
Figure 4U:
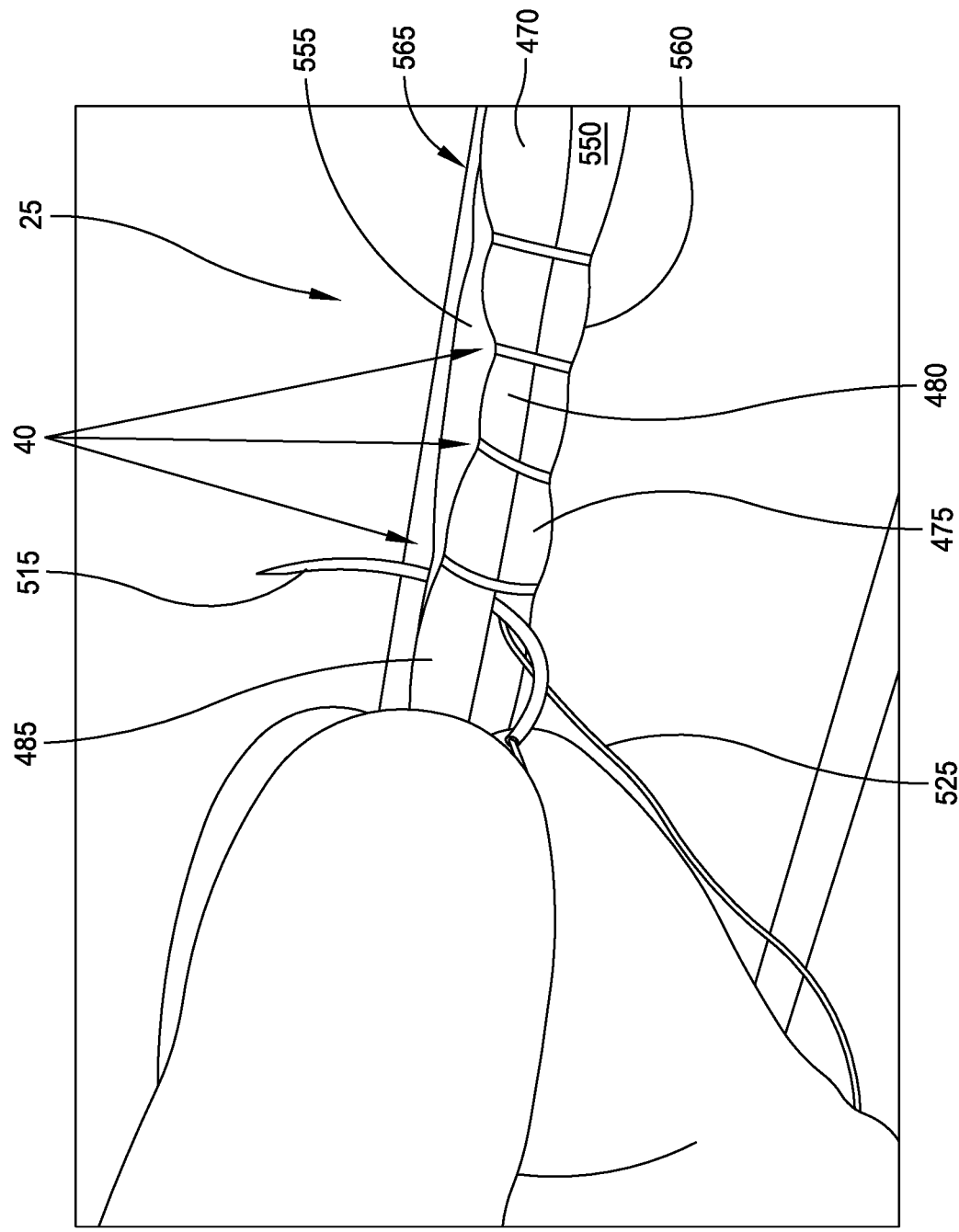
Figure 4V:
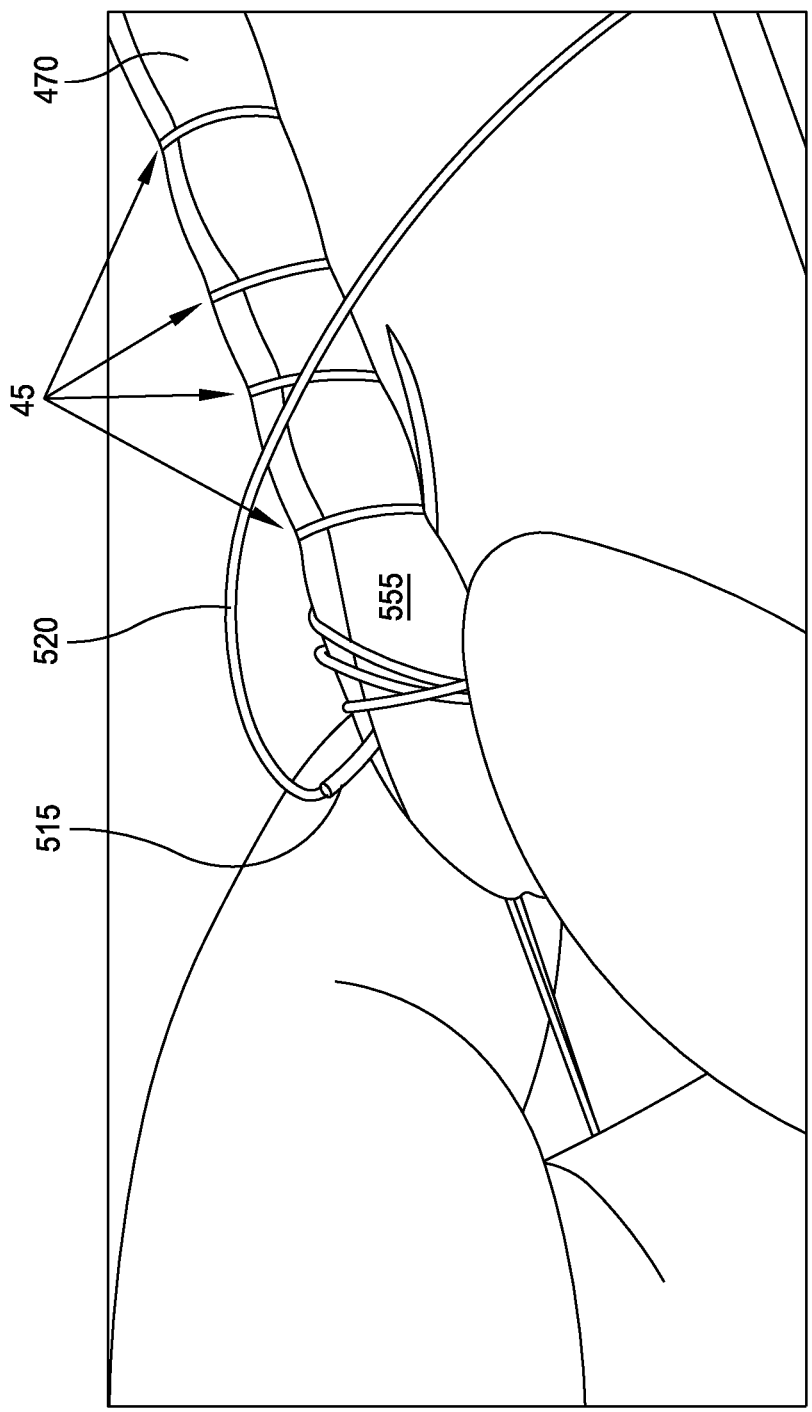
Figure 4W:
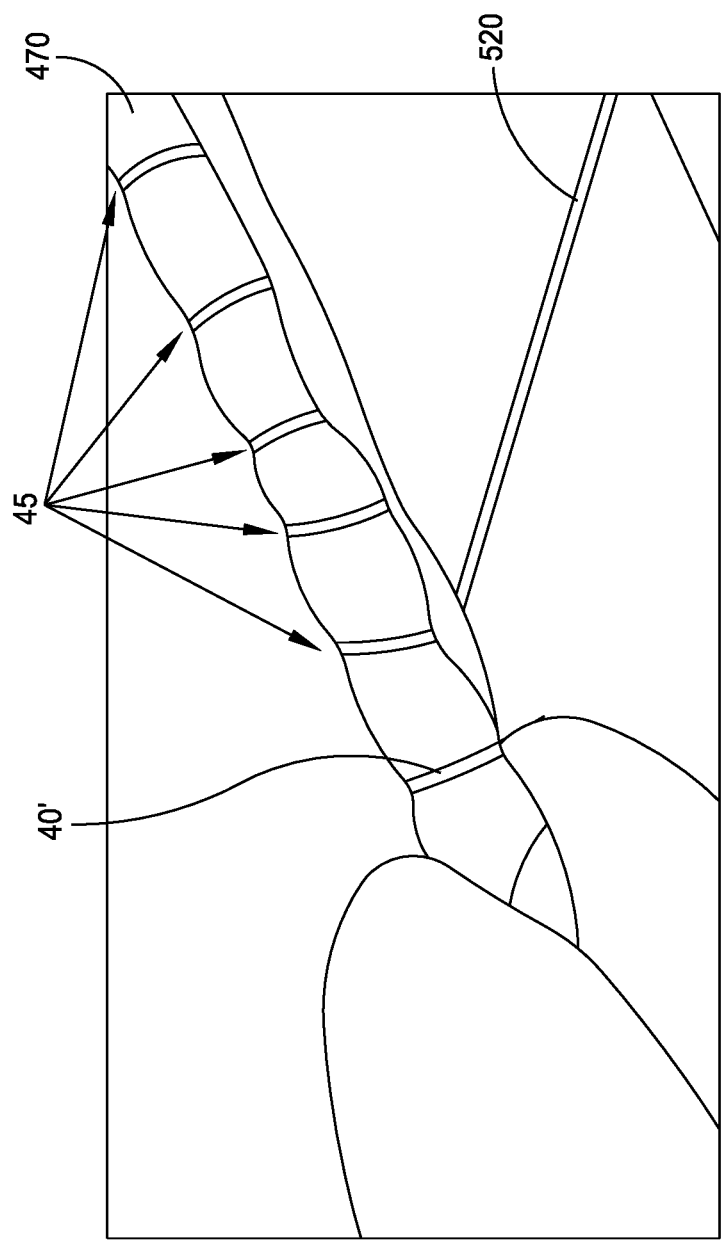
Figure 4X:
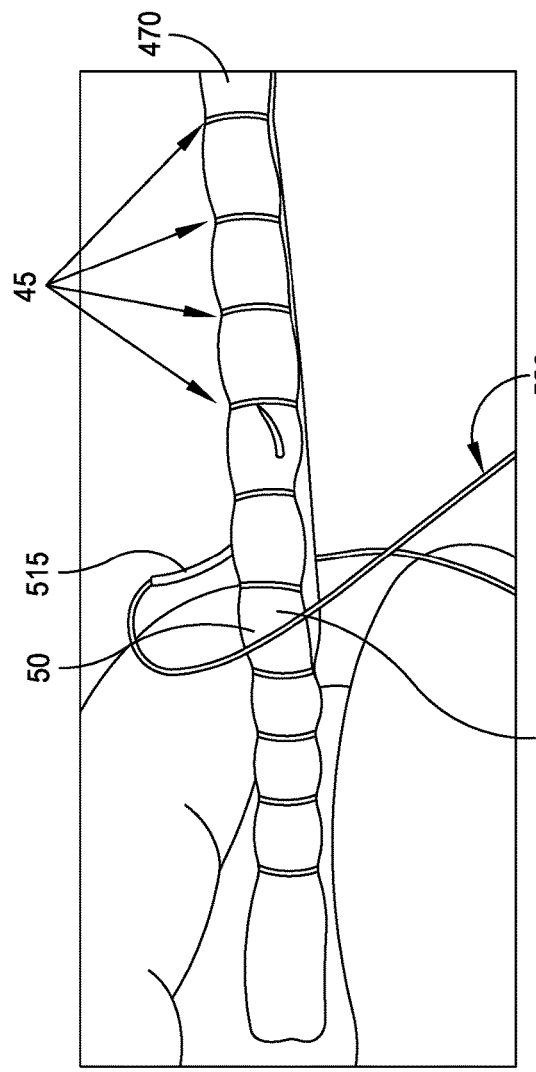
Figure 4Y:
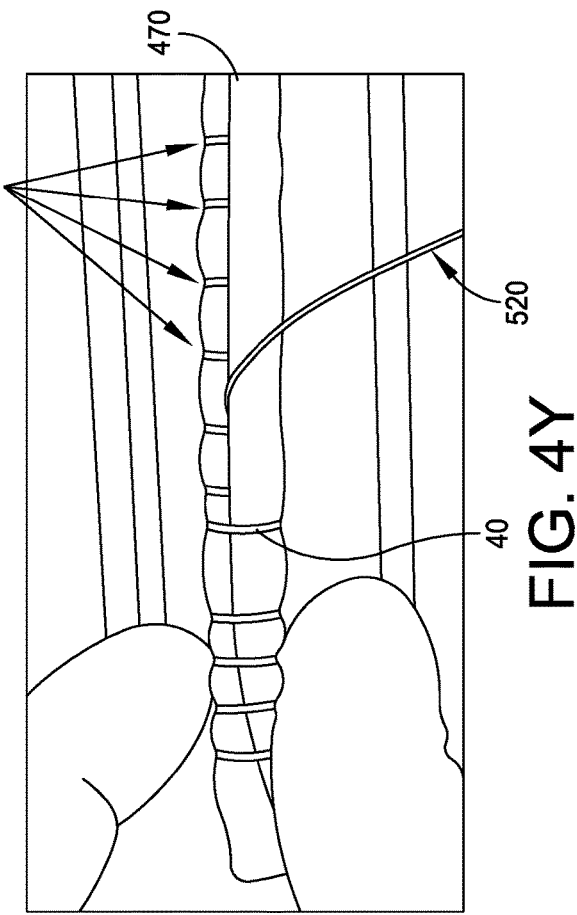
Figure 4Z:
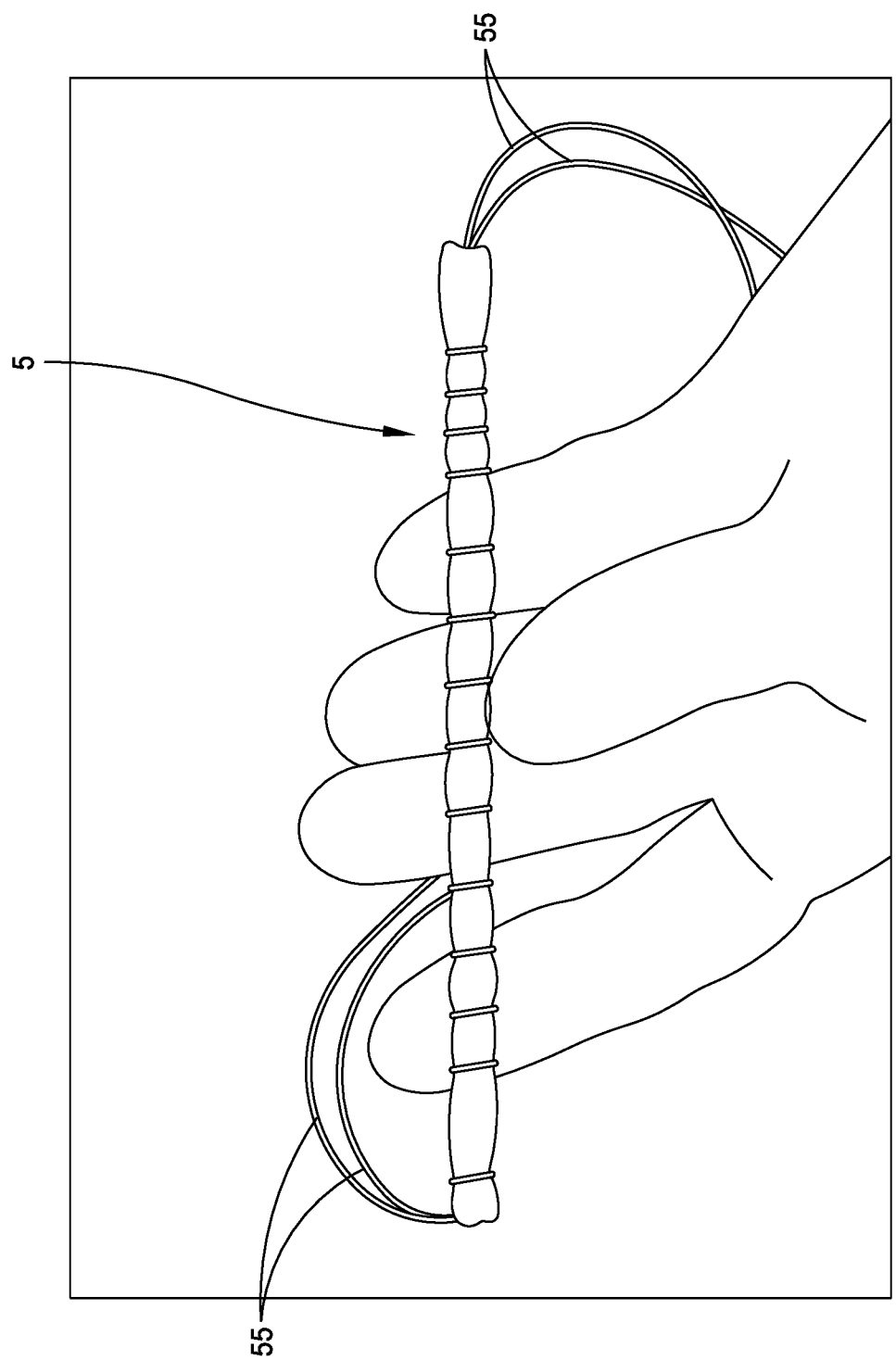
Figure 4A:
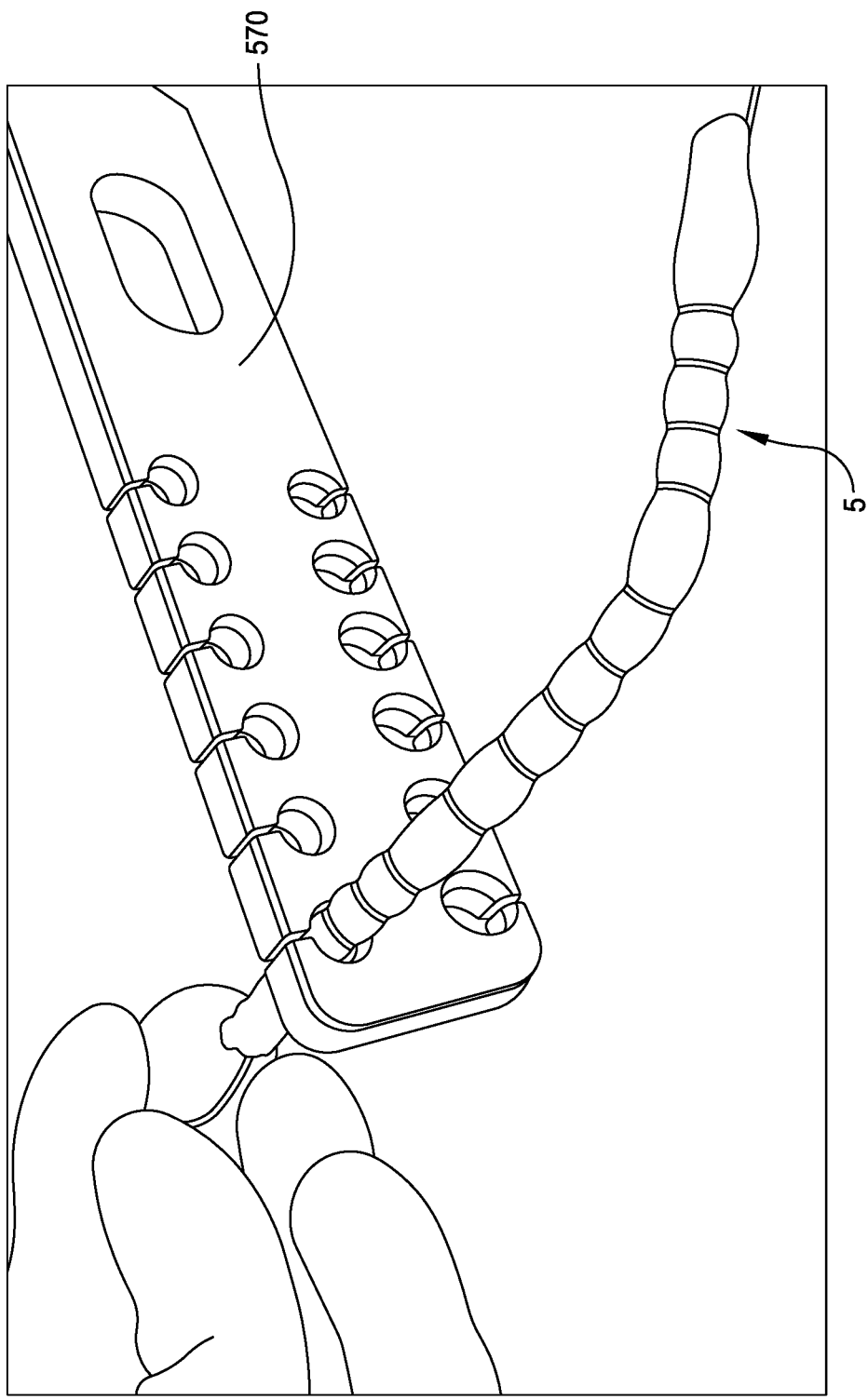

FIGS. 4A-4Z and 4AA illustrate the steps of an exemplary method of preparing an embodiment of the pre-sutured construct. Initially, the method may begin with obtaining a tissue portion 400 (FIG. 4A) (e.g., fascia) from a donor and evaluating the tissue portion for labrum replacement, repair, reconstruction, and augmentation standards. All excess soft tissue (e.g., connective tissue) not removed during cleansing may be removed prior to suturing.

Next, the technician may measure and cut the tissue portion into a pre-formed shape such as a rectangle, which may include placing the tissue onto a cutting board such that the tissue portion lies flat and the tissue fibers are oriented lengthwise (if applicable) relative to an allograft sizing board/block. Using the sizing board/block, the technician may measure and record a length of the tissue portion. This length measurement may be used to determine a size of the pre-sutured construct to be prepared, with minimum lengths, for example, of small at 80 mm, medium at 120 mm, and large at 160 mm. Using a combination of the sizing block and a ruler, the tissue portion may be adjusted/measured to achieve a rolled diameter between 5.0 to less than 6.5 mm, as shown in FIG. 4A, before a sterile marker 405 can be used to indicate a trim line, as shown in FIG. 4B, and the excess tissue is trimmed to create a tissue rectangle, shown in FIG. 4C, having front internal surface 410, a back external surface 415, a top edge 420, a bottom edge 425, a first edge 430, a second edge 435, and a uniform thickness or diameter of 5.0-6.5 mm when rolled.

Once cut into the pre-formed shape, the shape may be folded in preparation for suturing. Using the tissue rectangle, the technician may prepare a gate fold in the tissue by placing the tissue rectangle onto the cutting board with the external side of the tissue (e.g., fascia) facing down before first folding the top and bottom edges into the middle to form a gate fold 440, as shown in FIGS. 4E-4G, and then folding a now doubled bottom edge upward, leaving an approximate ¼ of the doubled tissue at the top uncovered or exposed to form an exposed fold portion 445 of a pre-folded graft 450, as shown in FIGS. 4H-4I.

Once folded into the pre-folded graft 450, the technician may initiate the suturing process using a needle threaded with an appropriate flexible strand such as, for example, suture material of rope or wire that is formed of natural or manmade materials that do not react negatively with human tissue. To begin, and as shown in FIG. 4J, the technician may suture a first construct end by inserting the needle through a back side of the exposed fold portion 445 of the pre-folded graft 450 at a point that is 3.0-5.0 mm from a first end (e.g., the right-side edge) of the pre-folded graft 450, through a front side of the of the exposed fold portion 445, and then creating a running stitch 455 from a top end 460 to a bottom end 465 of the pre-folded graft by repeatedly passing the needle through all layers of tissue.

Another running stich may then be created from the bottom end 465 to the top end 460, without crossing the sutures on the back side of the pre-folded graft 450. Next, the sutures may be pulled tight to remove all slack from the stitches and to gather the tissue into a rolled position, thereby forming a graft roll 470 having a bottom fold 475, a middle fold 480, and a top fold 485, where the exposed fold portion of the pre-folded graft forms the top fold 485, as shown in FIG. 4K. The suture ends 490 may be tied at the front side of the graft roll 470 into a square knot, with an additional knot to prevent sliding, to complete a first end stitch 495.

The steps described above to form the first construct end may be repeated on the opposing end to form a second construct end with a second end stitch 500, shown in FIG. 4L. In one embodiment and to assist with the suture pattern discussed below, the technician may create a double knot with the suture ends on both sides to form suture loops 55, as shown in FIGS. 1A, 2A, and 3A, such that the graft roll 470 may be positioned onto a graft preparation board 505 by attaching the suture loops to applicable and respective posts, with the top fold 485, and thus the exposed fold portion 445, positioned at the top, as shown in FIG. 4K. Suture loops 55 should be removed prior to implantation.

After completing the first and the second end stitches 495, 500, the technician may suture a whip stitch pattern along a length of the graft roll 470, beginning with the first adjustable region 15 and a first whip stitch 510 placed 5.0-10.0 mm inward from the end of tissue. To form the first whip stitch 510, the needle 515 may be passed into the graft roll 470 from an outside of the bottom fold 475 to an inside of the bottom fold 475, ensuring the needle passes between the bottom and the middle folds 475, 480 without piercing the middle fold, as shown in FIG. 4M. The suture 520 is pulled through, leaving 10.0-15.0 cm of a tail suture 525 (FIG. 4N) remaining, before being passed under the top fold 485 and exiting through the outside of the top fold 485 in direct alignment above the previous stitch, as shown in FIG. 4N.

Next, the needle 515 may be wrapped over the front of the graft roll 470, inserted through the outside of the bottom fold 475 adjacent to the tail suture 525, and passed through the bottom fold 475 to the inside between the bottom and the middle folds 480, 485, as shown in FIG. 4O, before the suture 525 is tightened to create a perpendicular stitch 530, or the first whip stitch 530 shown in FIG. 4P.

To continue the whip stitch pattern in the first adjustable region 15, the technician may insert the needle 515 a distance of 7 mm (±1 mm) inward from the previous stitch before passing the needle 515 from the front of the graft roll 470 under the top fold 485 between the middle and the top folds 480, 485, exiting through the outside of the top roll 485, as shown in FIG. 4Q. The needle may then be wrapped over the front of the graft roll 470, passed into the tissue through the outside of the bottom fold 475 in alignment with the previous stitch 535, and passed through the bottom fold 475 to the inside of the graft roll 470 between the bottom and the middle folds 475, 480, as shown in FIG. 4R, before the suture 520 has slack removed to create a perpendicular stitch 540. The steps of inserting the needle through the top fold at the 7 mm offset and passing the needle through the bottom fold in alignment with the previous stitch may be repeated as necessary until the whip stitches of the first adjustable region are complete, as required for the size of allograft construct being manufactured:

| Size | No. of Stitches | Offset; Length of Adjustable Region |
| --- | --- | --- |
| Small | 3 stitches | 7 mm (±1 mm); 12-16 mm total |
| Medium | 4 stitches | 7 mm (±1 mm); 20-24 mm total |
| Large | 4 stitches | 7 mm (±1 mm); 20-24 mm total |

For example, FIG. 4S shows four whip stitches 545 spanning approximately 20 mm for a medium construct.

To continue the whip stitch pattern through the central region 20, the technician may insert the needle 9 mm (±1 mm) beyond the previous stitch, or beyond the final whip stitch in the first adjustable region, before repeating the whip stitch pattern by passing the needle from the front of the graft roll 470 under the top fold between the middle and the top folds through to the outside of the top fold, wrapping over the front of the graft roll, passing the needle through the outside of the bottom fold in alignment with the previous stitch, through the bottom fold to the inside of the graft roll between the bottom and the middle folds, and tightening the suture to create a perpendicular stitch. This pattern may be repeated until the whip stitches of the central region are complete depending on the allograft construct size:

| Size | Central Region Length |
| --- | --- |
| Small | 35 mm-41 mm |
| Medium | 55 mm-61 mm |
| Large | 95 mm-101 mm |

For example, FIG. 4T shows six (6) whip stitches 40 in the central region 20 (adjacent the first adjustable region 15) spanning approximately 60 mm for a medium construct of the graft roll 470.

To complete the whip stitch pattern through the second adjustable region 25, the technician may insert the needle 515 a distance 7 mm (±1 mm) beyond the previous stitch 40, or beyond the final whip stitch in the central region, before repeating the whip stitch pattern by passing the needle from the front of the graft roll 470 under the top fold 485 between the middle and the top folds 480, 485 through to the outside of the top fold 485, wrapping over the front 550 of the graft roll 485, passing the needle 515 through the outside of the bottom fold 575 in alignment with the previous stitch, through the bottom fold to the inside of the graft roll between the bottom and the middle folds, and tightening the suture to create a perpendicular stitch. This pattern may be repeated until the whip stitches 40 of the second adjustable region 25 are complete depending on the allograft construct size:

| Size | No. of Stitches | Offset; Length of Adjustable Region |
|---|---|---|
| Small | 3 stitches | 7 mm (±1 mm); 12-16 mm total |
| Medium | 4 stitches | 7 mm (±1 mm); 20-24 mm total |
| Large | 4 stitches | 7 mm (±1 mm); 20-24 mm total |

On the final whip stitch, the needle 515 shall be passed from the front 550 of the graft roll 470 under the top fold 485, exiting through the outside of the top fold of the graft roll, as shown in FIG. 4U, before the tail suture 525 is secured and all of the whip stitches are tightened. Completion of the whip stitch pattern results in an intermediate allograft construct with a top 555, a bottom 560, the front 550, and a back 565.

Once the whip stitch pattern is complete, the technician may stitch a pattern of circumferential stitches 40', working from the second end region 30 adjacent to the final whip stitch, back through second adjustable region 25, through the central region 30, and through the first adjustable region 15 to the first end region 10. The suture pattern may begin with a set of triple circumferential stitches 40' in the second adjustable region 25. To start, the technician may wrap the suture 520 around the graft roll 470 over the final whip stitch, starting at the top of the intermediate allograft construct, and wrapping the suture 520 toward the back of the intermediate construct three times, before passing the needle from the top of the intermediate construct towards a bottom of the intermediate construct at the adjacent whip stitch, as shown in FIGS. 4V-4W, at which point the steps of triple wrapping the suture 520 and passing the needle 525 through the intermediate construct diagonally from the top of the intermediate construct towards the bottom of the construct at the next whip stitch may be repeated until a requisite number of triple circumferential stitches 40' have been completed in the second adjustable region. In an embodiment, the first circumferential stitch 40' is 3.0 wraps around the graft 470. The second, third, and fourth (if applicable) are 3.5 wraps being on the rough or sutured side:

| Small | 3 stitches |
|---|---|
| Medium | 4 stitches |
| Large | 4 stitches |

For the final triple circumferential stitch in the second adjustable region, the needle may be passed from the top of the intermediate construct and directed towards the bottom of the intermediate construct in a space between the last triple circumferential stitch and the adjacent whip stitch in the central region (not shown).

To form the circumferential stitches 45' in the central region 20, the technician may begin with a partial circumferential stitch 50 by wrapping the suture 520 from the bottom to the top of the intermediate construct and passing the needle 515 from the top of the intermediate construct and through to the bottom of the intermediate construct in a space between the next adjacent whip stitches (not shown). The technician may then wrap the suture 520 around the intermediate construct, beginning at the bottom and wrapping towards the front one and a half times, before passing the needle 515 from the top of the intermediate construct through to the bottom of the intermediate construct in a space between the next adjacent whip stitches, as shown in FIGS. 4X-4Y. This process of wrapping the suture 520 around the intermediate construct one and a half times before passing the needle 515 from the top of the intermediate construct through to the space between the next adjacent whip stitches may be repeated until stopping with the circumferential stitch 45' prior to the final whip stitch 45 in the central region. Then, a final partial circumferential stitch 50 may be formed by wrapping the suture to the top of the intermediate construct (i.e., ½ wrap) and passing the needle 515 from the top of the intermediate construct through to the bottom of the adjacent whip stitch 40 in the first adjustable region 15.

To complete the suture pattern, a set of triple circumferential stitches 40' may be formed in the first adjustable region. To start, the technician may wrap the suture 520 around the intermediate construct, starting at the top of the intermediate allograft construct, and wrapping the suture toward the back of the intermediate construct three times, before passing the needle 515 from the top of the intermediate construct towards a bottom of the intermediate construct at the adjacent whip stitch 40 in the first adjustable region, similar to the formation of the triple circumferential stitches 40' in the second adjustable region 25, discussed above in relation to FIGS. 4V-4W. In an embodiment, the first circumferential stitch 40' is 3.0 wraps around the graft 470. The second, third, and fourth (if applicable) are 3.5 wraps being on the rough or sutured side: The steps of triple wrapping the suture and passing the needle 515 through the intermediate construct diagonally from the top of the intermediate construct towards the bottom of the construct at the next whip stitch 40 may be repeated until the triple circumferential stitches 40', and indeed the entire suture pattern, are complete, and in the last triple stitch 40', the needle comes out adjacent to the tail suture 525:

| Small | 3 stitches |
|---|---|
| Medium | 4 stitches |
| Large | 4 stitches |

For the final triple circumferential stitch 40' in the first adjustable region, the needle 515 may be passed from the top of the intermediate construct, straight through to the bottom of the intermediate construct, next to the tail suture 525.

To complete the suture process, the technician may tie the remaining leading suture to the tail suture 525 using a square or surgeon's knot, repeating for a total of two knots. The tail suture 525 may then be trimmed before the needle is placed next to the surgeon's knots and the main, leading suture is passed through the tissue to complete the pre-sutured allograft construct 5 shown in FIG. 4Z. Any remaining suture may be trimmed. The completed pre-sutured allograft construct 5 may then be measured with a ruler for overall graft length between the outermost first and second end stitches, for a central length of the non-adjustable central region between the first and second adjustable regions, and for a diameter using a sizing block 570, as shown in FIG. 4AA:

| Size 5-5.5 | Passes through 5.5 but not 5 |
|---|---|
| Size 5.5-6 | Passes through 6 but not 5.5 |

While small, medium, and large sized constructs are described above, embodiments of the pre-sutured allograft 5 construct may have any appropriate overall length between 2 cm and 16 cm, may have adjustability between 2 cm and 16 cm, and may have diameters ranging between 4 mm and 8 mm.

Figure 5:
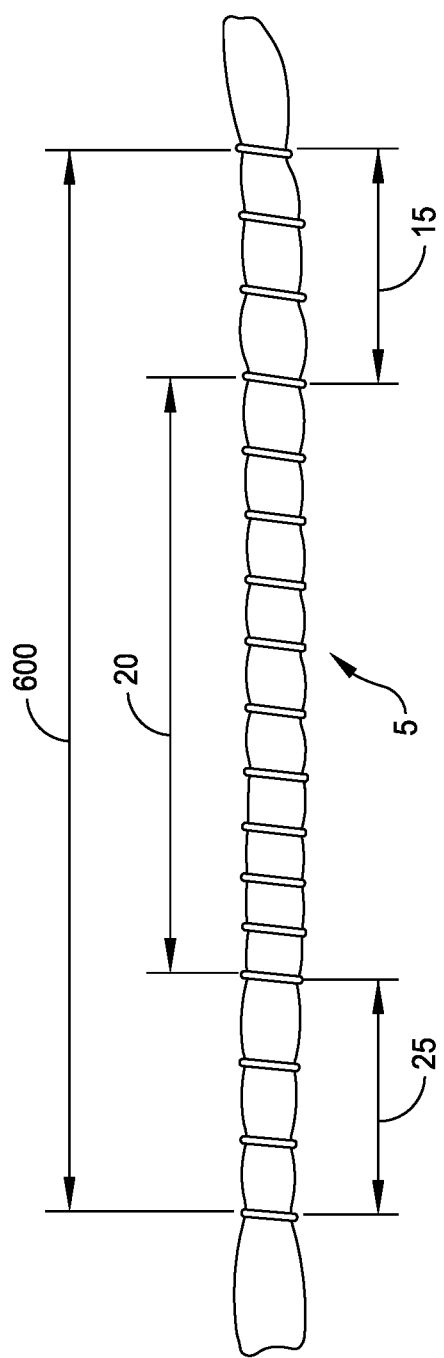
FIG. 5 illustrates the pre-sutured allograft with an overall length including adjustable regions and a center region.

With reference to FIG. 5, there is shown pre-suture allograft 5 with an overall length 600 extending from adjustable region 15, through the length of center region 20, and through adjustable region 25.

Once the suturing process and the pre-sutured allograft construct is complete, the pre-sutured construct 5 may be packaged and then sterilized using electron beam (E-beam) irradiation to sterility assurance level (SAL) $10^{-6}$.

Embodiments of the pre-sutured allograft construct 5 described herein may be used in the surgical specialty of labrum repair, replacement, reconstruction, or augmentation in the hip or shoulder, and enable the surgeon practitioner to order the pre-sutured, but adjustable, construct in preparation for surgery, rather than requiring him or her to prepare a custom graft during the surgical procedure itself. Often, as measurement of a defect may be difficult, the pre-sutured, but adjustable, construct may be trimmed in place in the patient's joint. Embodiments of the pre-sutured constructed may be adjusted in the body, during the procedure the additional compression of the graft caused by the three circumferential stitches hold the diving suture (the suture that passes from the top of one stitch through the graft to the bottom of the next) in place. When the graft is cut, the suture does not unravel due to the compressed surrounding tissue holding the suture in place. This combines time and cost savings provided by the use of a pre-sutured construct with maximum flexibility via the adjustable nature of the pre-sutured graft. This may be 30-40 minutes of operating room time as well as enhance patient safety with less time in the operating room. In addition to reducing operating time with the patient on the operating table, a surgeon may work alone, without a second set of hands, to help with customization of the pre-sutured construct as surgeons may find skilled technicians difficult to retain for custom fabrication of custom grafts in the surgical theatre. The pre-sutured construct further provides reproducible results by providing a consistent and functional graft construct.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A pre-sutured allograft construct for repairing, replacing, reconstructing, or augmenting a patient's labrum, comprising:
    a folded tissue portion extending from a first end to a second end, the folded tissue portion forming a top fold, a middle fold, and a bottom fold; and
    a stitched pattern securing the folded tissue portion into a graft roll having an overall length extending from a first adjustable region, through a central region, and through a second adjustable region, the graft roll having a selectively adjustable length, and the graft roll having a fixed diameter, wherein:
    a continuous series of whip stitches extends from the first adjustable region, through the central region, and through the second adjustable region;
    a series of triple circumferential stitches overlays the continuous series of the whip stitches in the first and the second adjustable regions; and
    a series of circumferential stitches alternates with the continuous series of the whip stitches in the central region.

2. The pre-sutured allograft construct of claim 1, wherein the selectively adjustable length of the graft roll is provided by compression of the graft caused by the series of triple circumferential stitches overlaying the whip stitches so as to allow a cut through the graft roll in at least one of the first adjustable region and the second adjustable region, and the graft roll adjacent to the cut is configured to resist becoming unraveled in response to the compression provided by the folded tissue portion compressed by the series of triple circumferential stitches holding the suture in place.

3. The pre-sutured allograft construct of claim 1, wherein the fixed diameter is between 5.0 mm and 5.5 mm.

4. The pre-sutured allograft construct of claim 1, wherein the fixed diameter is between 5.5 mm and 6.0 mm.

5. The pre-sutured allograft construct of claim 1, wherein the overall length is approximately 6 cm.

6. The pre-sutured allograft construct of claim 1, wherein the overall length is 10 cm.

7. The pre-sutured allograft construct of claim 1, wherein the overall length is 14 cm.

8. The pre-sutured allograft construct of claim 1, wherein the adjustable length is between 4 cm and 6 cm.

9. The pre-sutured allograft construct of claim 1, wherein the adjustable length is between 6 cm and 10 cm.

10. The pre-sutured allograft construct of claim 1, wherein the adjustable length is between 10 cm and 14 cm.

11. A pre-sutured allograft construct for repairing, replacing, reconstructing, or augmenting a patient's labrum, comprising:
    a tissue roll extending from a first end to a second end, the tissue roll including a top fold, a middle fold, and a bottom fold; and
    a stitched pattern securing the tissue roll, the stitched pattern extending from a first adjustable region, through a central region, and through a second adjustable region, wherein:
    each of the first and the second adjustable regions comprises a series of triple circumferential stitches directly overlaying a corresponding series of whip stitches; and
    the central region comprises a series of circumferential stitches alternating with the series of the whip stitches.

12. The pre-sutured allograft construct of claim 11, wherein each of the first adjustable region and the second adjustable region are provided by compression caused by the series of triple circumferential stitches overlaying the whip stitches so as to allow a cut through the tissue roll in at least one of the first adjustable region and the second adjustable region, and the tissue roll adjacent to the cut is configured to resist becoming unraveled in response to the compression provided by the folded tissue portion compressed by the series of triple circumferential stitches holding the suture in place.

13. The pre-sutured allograft construct of claim 11, wherein the series of whip stitches include partial whip stitches.

14. The pre-sutured allograft construct of claim 11, wherein the tissue roll has a diameter between 5.0 mm and 5.5 mm.

15. The pre-sutured allograft construct of claim 11, wherein the tissue roll has a diameter between 5.5 mm and 6.0 mm.

16. The pre-sutured allograft construct of claim 11, wherein the tissue roll has an overall length of approximately 6 cm.

17. The pre-sutured allograft construct of claim 11, wherein the tissue roll has an overall length of approximately 10 cm.

18. The pre-sutured allograft construct of claim 11, wherein the tissue roll has an overall length of approximately 14 cm.

19. The pre-sutured allograft construct of claim 11, wherein the adjustable length is between 4 cm and 6 cm.

20. The pre-sutured allograft construct of claim 11, wherein the adjustable length is between 6 cm and 10 cm.

21. The pre-sutured allograft construct of claim 11, wherein the adjustable length is between 10 cm and 14 cm.

22. A pre-sutured allograft construct for repairing, replacing, reconstructing, or augmenting a patient's labrum, comprising:
- a tissue roll extending from a first end to a second end; and
- a stitched pattern securing the tissue roll, the stitched pattern extending through an adjustable region and an adjacent region, wherein:
- the adjustable region comprises a series of triple circumferential stitches directly overlaying a corresponding series of whip stitches; and
- the adjacent region comprises a series of circumferential stitches alternating with the series of the whip stitches.

\* \* \* \* \*